(12) United States Patent
Sasamoto

(10) Patent No.: US 8,441,529 B2
(45) Date of Patent: May 14, 2013

(54) ENDOSCOPE OBJECTIVE LENS UNIT AND ENDOSCOPE

(75) Inventor: Tsutomu Sasamoto, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/314,542

(22) Filed: Dec. 8, 2011

(65) Prior Publication Data

US 2012/0147164 A1 Jun. 14, 2012

Related U.S. Application Data

(63) Continuation of application No. PCT/JP2011/060911, filed on May 12, 2011.

(30) Foreign Application Priority Data

May 20, 2010 (JP) ................................. 2010-116526

(51) Int. Cl.
| | | |
|---|---|---|
| *A62B 1/04* | (2006.01) | |
| *G02B 21/02* | (2006.01) | |
| *G02B 13/04* | (2006.01) | |
| *G02B 9/00* | (2006.01) | |
| *G02B 9/64* | (2006.01) | |
| *G02B 9/62* | (2006.01) | |

(52) U.S. Cl.
USPC ............ 348/65; 359/656; 359/657; 359/658; 359/659; 359/753; 359/754; 359/755; 359/756

(58) Field of Classification Search ........................ None
See application file for complete search history.

(56) References Cited

U.S. PATENT DOCUMENTS

| | | | | |
|---|---|---|---|---|
| 2004/0240081 A1* | 12/2004 | Saito | ................ | 359/754 |
| 2006/0221457 A1* | 10/2006 | Murayama | ................ | 359/656 |
| 2008/0180809 A1 | 7/2008 | Igarashi | | |

FOREIGN PATENT DOCUMENTS

| | | |
|---|---|---|
| JP | 02-074912 | 3/1990 |
| JP | 06-308381 | 11/1994 |
| JP | 2004-061763 | 2/2004 |
| JP | 2006-051132 | 2/2006 |
| JP | 2006-113287 | 4/2006 |
| JP | 2007-249189 | 9/2007 |
| JP | 2008-107391 | 5/2008 |
| JP | 2008-268281 | 11/2008 |

OTHER PUBLICATIONS

Japanese Office Action dated Jan. 31, 2012 in corresponding Japanese Patent Application No. 2011-551138.

* cited by examiner

*Primary Examiner* — Joseph Ustaris
*Assistant Examiner* — Frederick Bailey
(74) *Attorney, Agent, or Firm* — Scully, Scott, Murphy & Presser, P.C.

(57) ABSTRACT

An endoscope objective lens unit includes a front lens group and a rear lens group with a diaphragm interposed therebetween. The front lens group includes a first lens and a second lens, and the rear lens group includes a third lens, a fourth lens and a fifth lens. The endoscope objective lens unit satisfies following expressions (1A) to (4): (1A) $-3 < SF -1$; (2) $-3 < Fr/Ff < -1.1$; (3) $-1.6 < Ff/f < -0.6$; and (4) $Ff/f1 < 1.6$, where SF is a shape factor, Ff is a focal length of the front lens group, Fr is a focal length of the rear lens group, f is a focal length of the entire unit, and f1 is a focal length of the first lens.

8 Claims, 27 Drawing Sheets

ENDOSCOPE OBJECTIVE LENS UNIT AND ENDOSCOPE

CROSS REFERENCE TO RELATED APPLICATION

This application is a continuation application of PCT/JP2011/060911 filed on May 12, 2011 and claims benefit of Japanese Application No. 2010-116526 filed in Japan on May 20, 2010, the entire contents of which are incorporated herein by this reference.

BACKGROUND OF THE INVENTION

1. Field of the Invention

The present invention relates to an endoscope objective lens unit arranged at a distal end portion of an endoscope and an endoscope including the endoscope objective lens unit.

2. Description of the Related Art

In a medical field, endoscopes are used for, e.g., treatment/diagnosis of sites that are difficult to observe from outside of bodies of patients. There is a large demand for a further diameter reduction in endoscopes with small diameters, represented by nasal endoscopes. Reduction in diameter of endoscopes largely depends on development of small-sized image pickup devices such as CCDs, and pixel pitches of image pickup devices are reduced year by year. Accompanied by such reduction, there is a need for endoscope objective lens units (hereinafter also referred to as "lens units") to provide satisfactory performance while achieving size reduction, and various types of configurations have been developed.

For example, in Japanese Patent Application Laid-Open Publication No. 6-308381, the present applicant discloses an endoscope objective lens including a front lens group and a rear lens group with a diaphragm interposed therebetween, in which the front lens group includes a first group of negative lenses and a second group having a positive refractive power in this order from an object side, the second group has a shape including a surface having a small curvature radius provided on an image side, the rear lens group includes a positive single lens and a cemented lens of a positive lens and a negative lens, and the endoscope objective lens satisfies a predetermined condition.

Meanwhile, in Japanese Patent Application Laid-Open Publication No. 2006-51132, the present applicant also discloses a lens unit including a lens that includes a high refractive index material that exhibits excellent sterilization durability.

SUMMARY OF THE INVENTION

An endoscope objective lens unit according to an embodiment of the present invention includes a front lens group and a rear lens group with a diaphragm interposed therebetween. The front lens group includes a first lens having a negative refractive power and a second lens having a positive refractive power in this order from an object side. The rear lens group includes a third lens having a positive refractive power, and a fourth lens having a positive refractive power and a fifth lens having a negative refractive power, the fourth lens and the fifth lens being cemented to each other. The endoscope objective lens unit satisfies expressions (1A), (2), (3) and (4) below:

$$-3 < SF \leq -1; \tag{1A}$$

$$-3.0 < Fr/Ff < -1.1; \tag{2}$$

$$-1.6 < Ff/f < -0.6; \text{ and} \tag{3}$$

$$Ff/f1 < 1.6, \tag{4}$$

where SF is a shape factor of $(R2+R1)/(R2-R1)$, in which R1 is an object-side curvature radius of the second lens and R2 is an image-side curvature radius of the second lens, Ff is a focal length of the front lens group, Fr is a focal length of the rear lens group, f is a focal length of the entire unit, and f1 is a focal length of the first lens.

Also, an endoscope according to another embodiment of the present invention includes the endoscope objective lens unit, and an image pickup device that picks up an image provided by the endoscope objective lens unit.

BRIEF DESCRIPTION OF THE DRAWINGS

FIG. 24E is a field curvature diagram of the lens unit according to example 24;

FIG. 25A is a cross-sectional diagram taken along an optical axis for illustrating a lens unit according to example 25;

FIG. 25B is a spherical aberration diagram for illustrating the lens unit according to example 25;

FIG. 25C is a coma aberration diagram (M) for illustrating the lens unit according to example 25;

FIG. 25D is a coma aberration diagram (S) for illustrating the lens unit according to example 25;

FIG. 25E is a field curvature diagram for illustrating the lens unit according to example 25;

FIG. 26A is a cross-sectional diagram taken along an optical axis for illustrating a lens unit according to example 26;

FIG. 26B is a spherical aberration diagram for illustrating the lens unit according to example 26;

FIG. 26C is a coma aberration diagram (M) for illustrating the lens unit according to example 26;

FIG. 26D is a coma aberration diagram (S) for illustrating the lens unit according to example 26;

FIG. 26E is a field curvature diagram for illustrating the lens unit according to example 26; and FIG. 27 is a configuration diagram of an endoscope according to example 27.

DETAILED DESCRIPTION OF THE PREFERRED EMBODIMENTS

Figure 1A:
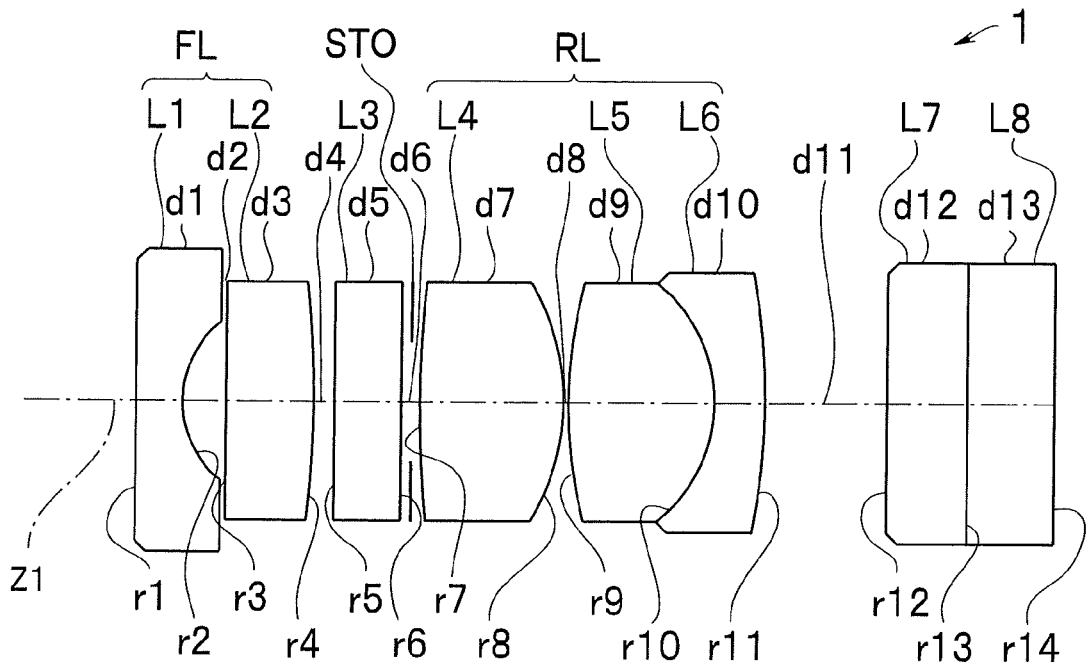
FIG. 1A is a cross-sectional diagram taken along an optical axis for illustrating a lens unit according to example 1.

An endoscope objective lens unit according to an embodiment of the present invention is described below.

1. The endoscope objective lens unit includes a front lens group and a rear lens group with a diaphragm interposed therebetween. The front lens group includes a first lens having a negative refractive power and a second lens having a positive refractive power in this order from an object side. The rear lens group includes a third lens having a positive refractive power, and a fourth lens having a positive refractive power and a fifth lens having a negative refractive power, the fourth lens and the fifth lens being cemented to each other. The endoscope objective lens unit satisfies expressions (1), (2), (3) and (4) below:

$$-6 < SF < 0; \tag{1}$$

$$-3.0 < Fr/Ff < -1.1; \tag{2}$$

$$-1.6 < Ff/f < -0.6; \text{ and} \tag{3}$$

$$Ff/f1 < 1.6, \tag{4}$$

where SF is a shape factor of (R2+R1)/(R2−R1), in which R1 is an object-side curvature radius of the second lens and R2 is an image-side curvature radius of the second lens, Ff is a focal length of the front lens group, Fr is a focal length of the rear lens group, f is a focal length of the entire unit, and f1 is a focal length of the first lens.

Condition (1) is a condition for designating a direction of a surface for favorable correction of a chromatic aberration of magnification. Satisfaction of condition (1) enables favorable correction of a chromatic aberration of magnification. With a value less than the lower limit of condition (1), although a chromatic aberration of magnification can favorably be corrected with the total length kept small, i.e., the reduced size maintained, it is difficult to correct other aberrations. With a value exceeding the upper limit of condition (1), it is difficult to correct a chromatic aberration of magnification.

Furthermore, satisfaction of condition (1A) below instead of condition (1) enables more favorable correction of a chromatic aberration of magnification:

$$-3 < SF \leq -1. \tag{1A}$$

Furthermore, satisfaction of condition (1B) below instead of condition (1A) enables more favorable correction of a chromatic aberration of magnification:

$$-3 < SF < -1.2. \tag{1B}$$

Conditions (2) and (3) are conditions for achieving size reduction. With a value less than the lower limit of condition (2), a lens unit meeting the recent size reduction cannot be provided, and with a value exceeding the upper limit of condition (2), although a small-sized lens unit can be supplied, it is difficult to correct other aberrations.

With a value less than the lower limit of condition (3), the total length of the lens unit is long, disabling supply of a small-sized lens unit, and with a value exceeding the upper limit of condition (3), although a small-sized lens unit can be supplied, it is difficult to correct coma aberrations occurred in the front lens group.

Furthermore, satisfaction of condition (2A) below instead of condition (2) enables further size reduction:

$$-1.8<Fr/Ff<-1.2. \quad (2A)$$

Furthermore, satisfaction of condition (2B) below instead of condition (2A) enables further size reduction:

$$-1.75<Fr/Ff<-1.3. \quad (2B)$$

Furthermore, satisfaction of condition (3A) below instead of condition (3) enables further size reduction:

$$-1.5<Fr/f<-0.9. \quad (3A)$$

Furthermore, satisfaction of condition (3B) below instead of condition (3A) enables further size reduction:

$$-1.4<Fr/f<-0.95. \quad (3B)$$

Condition (4) is a condition for favorably correcting a field curvature with reduction in size of the lens unit taken into account. With a value exceeding the upper limit of condition (4), excessive field curvature correction is provided, resulting in difficulty in correction of a field curvature.

Furthermore, satisfaction of condition (4A) below instead of condition (4) enables more favorable field curvature correction:

$$Ff/f1<1.51. \quad (4A)$$

Furthermore, satisfaction of condition (4B) below instead of condition (4A) enables more favorable field curvature correction:

$$Ff/f1<1.39. \quad (4B)$$

Furthermore, the lens unit according to the embodiment of the present invention enables easy provision of a long back focal length. The lens unit according to the embodiment, which has a long back focal length, enables a prism to be disposed immediately in front of a CCD of an image pickup device to place the CCD horizontally. In other words, as in examples 6, 7, 10 or 18, which are described later, a lens unit including an optical member L7 having a long optical path, the optical member being joined to a glass lid of the CCD, can use a right angle prism as the optical member L7, enabling provision of what is called a horizontally-arranged CCD. In other words, the lens unit according to the embodiment of the present invention enables easy provision of a horizontally-arranged CCD.

2. The lens unit according to section 1 above, in which a refractive index n1 (for an e-line) of a material of the first lens satisfies expression (5) below:

$$n1>2. \quad (5)$$

It is preferable to satisfy condition (5) because the power of the front lens group can easily be increased.

3. The lens unit according to section 1 or 2 above, in which the material of the first lens satisfies expression (6) below:

$$n1 \times Hk>2000, \quad (6)$$

where n1 is a refractive index (for an e-line) and Hk is a Knoop hardness (N/mm$^2$).

Use of the material satisfying condition (6) enables provision of a lens unit including an outer surface lens (first lens) having resistance to cracking and lens scratching.

4. The material of the first lens includes yttria-stabilized zirconia.

Yttria-stabilized zirconia (YSZ) is a specific example of the material satisfying section 3 above. In other words, in YSZ, n1=2.1825, Hk=1200 N/mm$^2$ and n1×Hk=2617>2000.

An endoscope according to the present invention includes the endoscope objective lens unit according to sections 1 to 4 above.

Next, examples of the lens unit according to the present invention will be indicated.

EXAMPLE 1

Numerical data, etc. of optical members included in a lens unit 1 according to example 1 are indicated below. In the numerical data, r is a curvature radius of each surface, d is a thickness of each optical member or an air space between the respective optical members, n is an refractive index of each optical member for an e-line, ν is an Abbe number of each optical member for the e-line, and FNO represent an F-number. The unit of r and d is mm.

These signs are used in common to numerical data, etc. of later-described other examples.

Numerical data in example 1 is indicated below.

TABLE 1

| r1 = ∞ | d1 = 0.4000 | n1 = 1.88815 | ν1 = 40.76 |
|---|---|---|---|
| r2 = 0.8439 | d2 = 0.3813 | n2 = 1.85504 | ν2 = 23.78 |
| r3 = ∞ | d3 = 0.7337 | n3 = 1.51564 | ν3 = 75.00 |
| r4 = −9.6109 | d4 = 0.1912 | n4 = 1.83932 | ν4 = 37.16 |
| r5 = ∞ | d5 = 0.5652 | n5 = 1.69979 | ν5 = 55.53 |
| r6 = ∞(STO) | d6 = 0.1599 | n6 = 1.93429 | ν6 = 18.90 |
| r7 = 9.4824 | d7 = 1.2442 | n7 = 1.51825 | ν7 = 64.14 |
| r8 = −1.9686 | d8 = 0.0529 | n8 = 1.61379 | ν8 = 50.20 |
| r9 = 3.9815 | d9 = 1.2483 | | |
| r10 = −1.2679 | d10 = 0.4334 | | |
| r11 = −5.8682 | d11 = 1.0546 | | |
| r12 = ∞ | d12 = 0.7000 | | |
| r13 = ∞ | d13 = 0.7500 | | |
| r14 = ∞ | | | |

FNO = 4.68
Focal length of entire unit: f = 1 mm, image height = 0.946 mm, object distance = 20 mm, angle of view = 128.05°
Fr = 1.617 mm,
Ff = −1.123 mm,
f1 = −0.950 mm FIG. 1A is a configuration diagram of the lens unit 1 according to the present example, and FIGS. 1B to 1E are aberration diagrams of the lens unit 1. As illustrated in FIG. 1A, a lens unit 1 includes a front lens group FL and a rear lens group RL with a diaphragm STO interposed therebetween. The front lens group FL includes a first lens L1 having a negative refractive power and a second lens L2 having a positive refractive power in this order from an object side. The rear lens group RL includes a third lens L4 having a positive refractive power, and a fourth lens L5 having a positive refractive power and a fifth lens L6 having a negative refractive power, the fourth lens L5 and the fifth lens L6 being cemented to each other. In FIG. 1A, r14 is an image pickup surface of an image pickup device such as a CCD.

In FIG. 1A, an optical member L3 is a filter, particularly preferably, an infrared cut filter. In the later-described other examples, an optical member L3 is a functional filter: however, use of a color filter instead of an infrared cut filter enables variation in color-reproducibility of an endoscopic image.

Furthermore, a plurality of filters, for example, three infrared cut filters may be disposed at a position of the optical member L3 if it is possible. Furthermore, filters having different functions, for example, an infrared cut filter and a notch filter, may be disposed, or an infrared cut filter, a color filter and a notch filter may be disposed.

A position where the filter is arranged is not limited the position of the optical member L3. For example, it is possible to use normal transparent glass as the optical member L3 and dispose an infrared cut filter at a position that is different from the position of the optical member L3. In other words, for a lens unit with no filter disposed in later-described examples, it is possible to arbitrarily dispose a necessary filter in an air space.

Furthermore, it is preferable that the filter include a functional film, such as a YAG laser cut film, formed at least one surface thereof, and it is particularly preferable that the filter include a functional film, such as a YAG laser cut film or an LD laser cut film, formed at another surface thereof. In other words, it is preferable that the filter include a functional film including an antireflective film formed at one surface or each of opposite surfaces thereof. Alternatively, plural functional films having different functions may be stacked on one of surfaces of the filter.

Figures 1B, 1C, 1D, 1E:
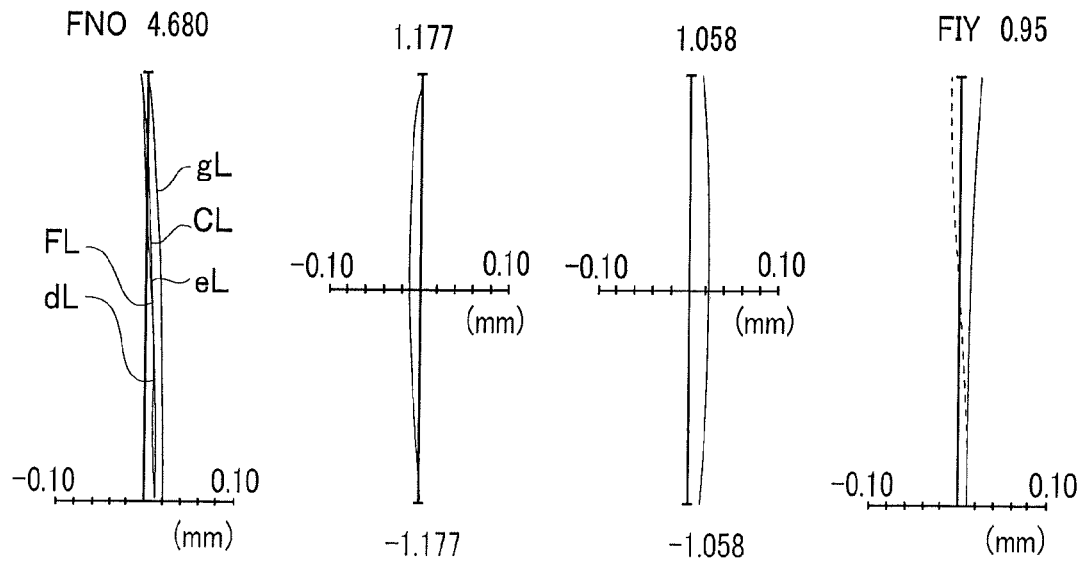
FIG. 1B is a spherical aberration diagram for illustrating the lens unit according to example 1.
FIG. 1C is a coma aberration diagram (M) for illustrating the lens unit according to example 1.
FIG. 1D is a coma aberration diagram (S) for illustrating the lens unit according to example 1.
FIG. 1E is a field curvature diagram for illustrating the lens unit according to example 1.

FIG. 1B indicates spherical aberration, FIGS. 1C and 1D each indicate coma aberration, and FIG. 1E indicates a field curvature (field aberration). In FIG. 1B, symbols indicate measured wavelength lines: (CL) indicates 656.27 nm, i.e., a C-line; (dL) indicates 587.56 nm, i.e., a d-line; (eL) indicates 546.07 nm, i.e., an e-line; (F) indicates 486.13 nm, i.e., an F-line; and (g) indicates 435.83 nm, i.e., a g-line. FIG. 1C indicates coma aberration ΔM (meridional) for the e-line, and FIG. 1D indicates a coma aberration ΔS (sagittal). In FIG. 1E, ΔS is indicated by a solid line and ΔM is indicated by a dashed line. The same applies to the following aberration diagrams.

EXAMPLE 2

Numerical data, etc. of optical members included in a lens unit 2 according to example 2 are indicated below.

TABLE 2

| | | | |
|---|---|---|---|
| r1 = ∞ | d1 = 0.4030 | n1 = 1.88815 | ν1 = 40.76 |
| r2 = 0.8788 | d2 = 0.4814 | n2 = 1.85504 | ν2 = 23.78 |
| r3 = −10.0294 | d3 = 0.7668 | n3 = 1.51564 | ν3 = 75.00 |
| r4 = −4.696 | d4 = 0.2364 | n4 = 1.83932 | ν4 = 37.16 |
| r5 = ∞ | d5 = 0.5676 | n5 = 1.69979 | ν5 = 55.53 |
| r6 = ∞(STO) | d6 = 0.1612 | n6 = 1.93429 | ν6 = 18.90 |
| r7 = 9.5228 | d7 = 1.2725 | n7 = 1.51825 | ν7 = 64.14 |
| r8 = −2.0903 | d8 = 0.0531 | n8 = 1.61379 | ν8 = 50.20 |
| r9 = 4.3821 | d9 = 1.2536 | | |
| r10 = −1.2663 | d10 = 0.4353 | | |
| r11 = −6.0967 | d11 = 0.8910 | | |
| r12 = ∞ | d12 = 1.4000 | | |
| r13 = ∞ | d13 = 0.3000 | | |
| r14 = ∞ | | | |

Figure 2A:
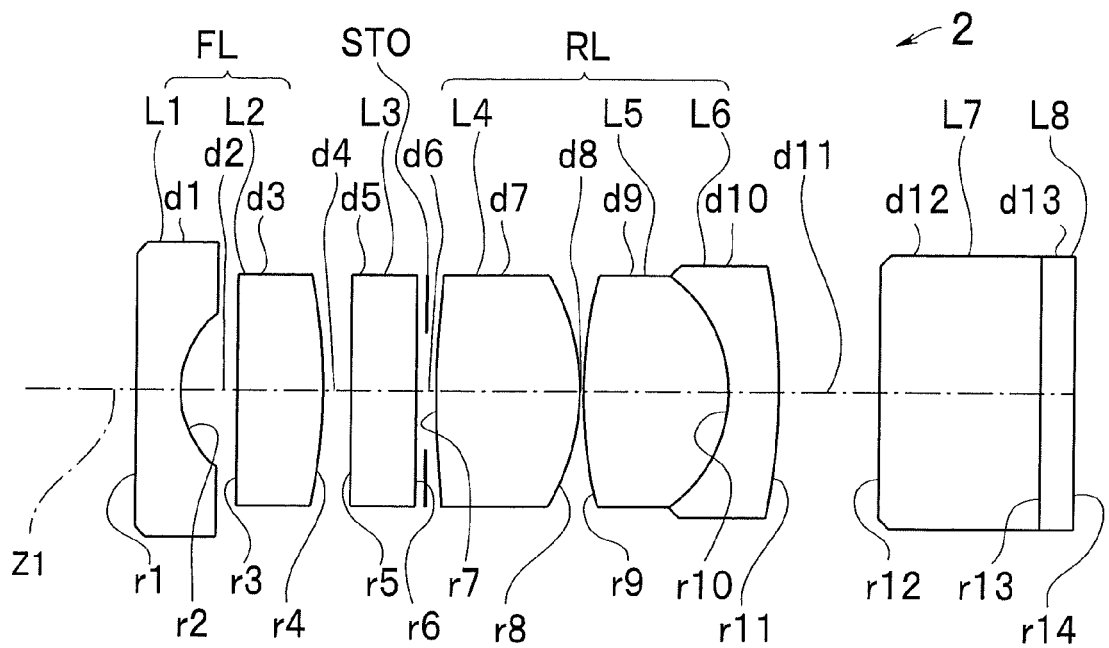
FIG. 2A is a cross-sectional diagram taken along an optical axis for illustrating a lens unit according to example 2.
Figures 2B, 2C, 2D, 2E:
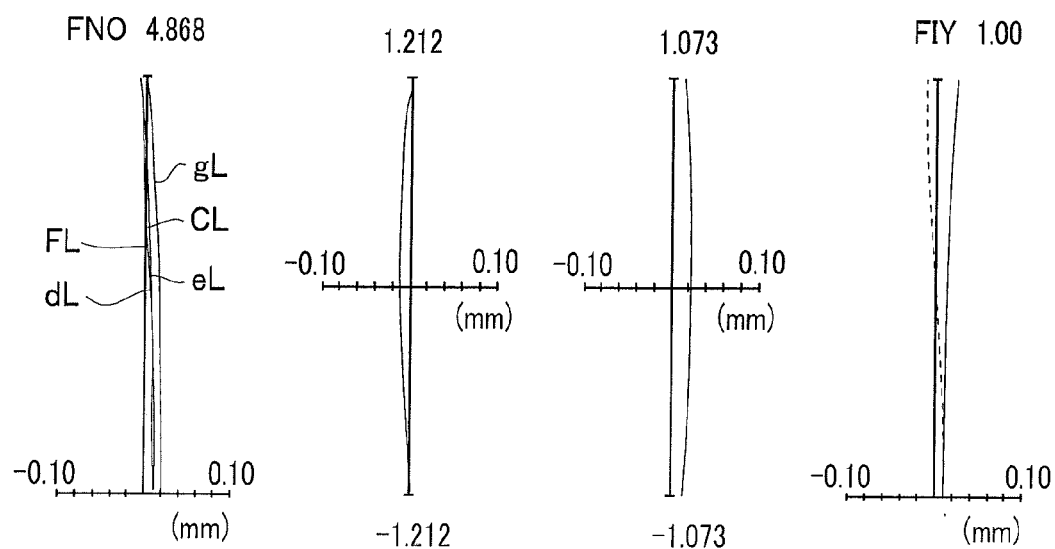
FIG. 2B is a spherical aberration diagram for illustrating the lens unit according to example 2.
FIG. 2C is a coma aberration diagram (M) for illustrating the lens unit according to example 2.
FIG. 2D is a coma aberration diagram (S) for illustrating the lens unit according to example 2.
FIG. 2E is a field curvature diagram for illustrating the lens unit according to example 2.

FNO = 4.868
Focal length of entire unit: f = 1 mm, image height = 1 mm, object distance = 17 mm, angle of view = 140.05°
Fr = 1.729 mm,
Ff = −1.280 mm,
fl = −0.989 mm FIG. 2A is a configuration diagram of the lens unit 2 according to the present example, and FIGS. 2B to 2E are aberration diagrams of the lens unit 2.

EXAMPLE 3

Numerical data, etc. of optical members included in a lens unit 3 according to example 3 are indicated below.

TABLE 3

| | | | |
|---|---|---|---|
| r1 = ∞ | d1 = 0.4072 | n1 = 1.88815 | ν1 = 40.76 |
| r2 = 0.8765 | d2 = 0.5877 | n2 = 1.85504 | ν2 = 23.78 |
| r3 = −10.1323 | d3 = 0.7329 | n3 = 1.51564 | ν3 = 75.00 |
| r4 = −4.2879 | d4 = 0.1773 | n4 = 1.83932 | ν4 = 37.16 |
| r5 = ∞ | d5 = 0.5734 | n5 = 1.69979 | ν5 = 55.53 |
| r6 = ∞(STO) | d6 = 0.1629 | n6 = 1.93429 | ν6 = 18.90 |
| r7 = 9.6206 | d7 = 1.2981 | n7 = 1.51825 | ν7 = 64.14 |
| r8 = −2.0932 | d8 = 0.0537 | n8 = 1.61379 | ν8 = 50.20 |
| r9 = 4.598 | d9 = 1.2665 | | |
| r10 = −1.2298 | d10 = 0.4398 | | |
| r11 = −6.2165 | d11 = 0.9322 | | |
| r12 = ∞ | d12 = 1.2969 | | |
| r13 = ∞ | d13 = 0.3546 | | |
| r14 = ∞ | | | |

Figure 3A:
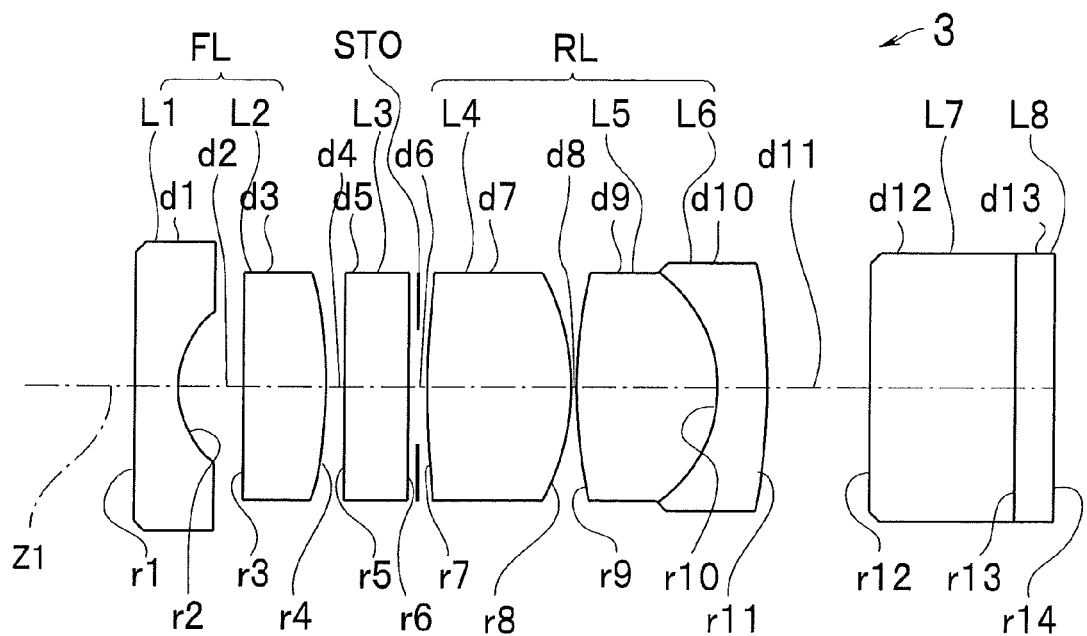
FIG. 3A is a cross-sectional diagram taken along an optical axis for illustrating a lens unit according to example 3.
Figures 3B, 3C, 3D, 3E:
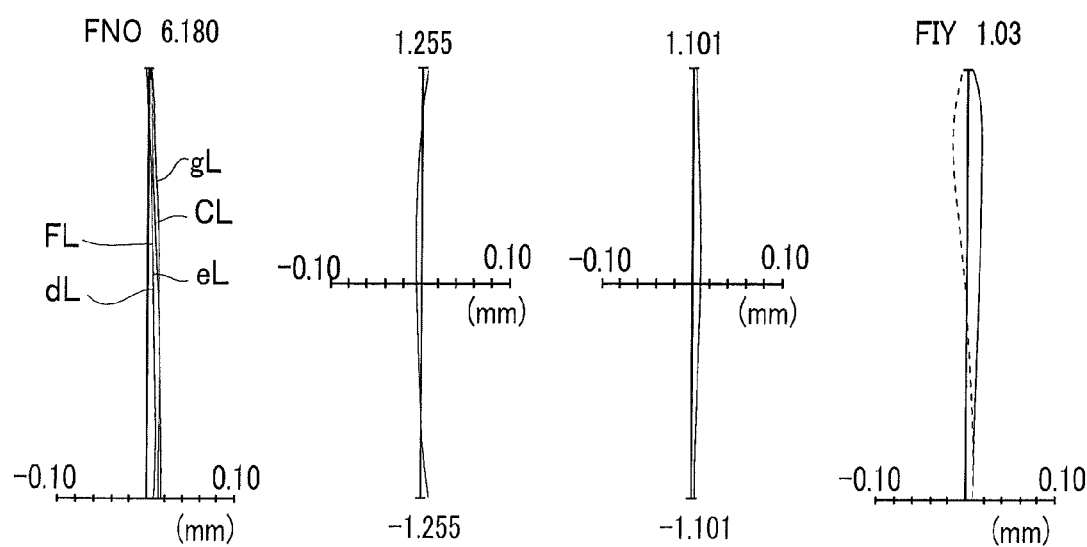
FIG. 3B is a spherical aberration diagram for illustrating the lens unit according to example 3.
FIG. 3C is a coma aberration diagram (M) for illustrating the lens unit according to example 3.
FIG. 3D is a coma aberration diagram (S) for illustrating the lens unit according to example 3.
FIG. 3E is a field curvature diagram for illustrating the lens unit according to example 3.

FNO = 6.18
Focal length of entire unit: f = 1 mm, image height = 1.33 mm, object distance = 10 mm, angle of view = 147.36°
Fr = 1.766 mm,
Ff = −1.353 mm,
fl = −0.987 mm FIG. 3A is a configuration diagram of the lens unit 3 according to the present example, and FIGS. 3B to 3E are aberration diagrams of the lens unit 3.

EXAMPLE 4

Numerical data, etc. of optical members included in a lens unit 4 according to example 4 are indicated below.

TABLE 4

| | | | |
|---|---|---|---|
| r1 = ∞ | d1 = 0.4054 | n1 = 1.88815 | ν1 = 40.76 |
| r2 = 0.8755 | d2 = 0.5851 | n2 = 1.85504 | ν2 = 23.78 |
| r3 = −11.9923 | d3 = 0.6742 | n3 = 1.51564 | ν3 = 75.00 |
| r4 = −4.9781 | d4 = 0.1924 | n4 = 1.83932 | ν4 = 37.16 |
| r5 = ∞ | d5 = 0.5708 | n5 = 1.69979 | ν5 = 55.53 |
| r6 = ∞(STO) | d6 = 0.1614 | n6 = 1.93429 | ν6 = 18.90 |
| r7 = 9.5779 | d7 = 1.3297 | n7 = 1.51825 | ν7 = 64.14 |
| r8 = −2.1418 | d8 = 0.0605 | n8 = 1.61379 | ν8 = 50.20 |
| r9 = 4.7428 | d9 = 1.2609 | | |
| r10 = −1.2532 | d10 = 0.4378 | | |
| r11 = −5.2230 | d11 = 0.8500 | | |
| r12 = ∞ | d12 = 1.4485 | | |
| r13 = ∞ | d13 = 0.5015 | | |
| r14 = ∞ | | | |

Figure 4A:
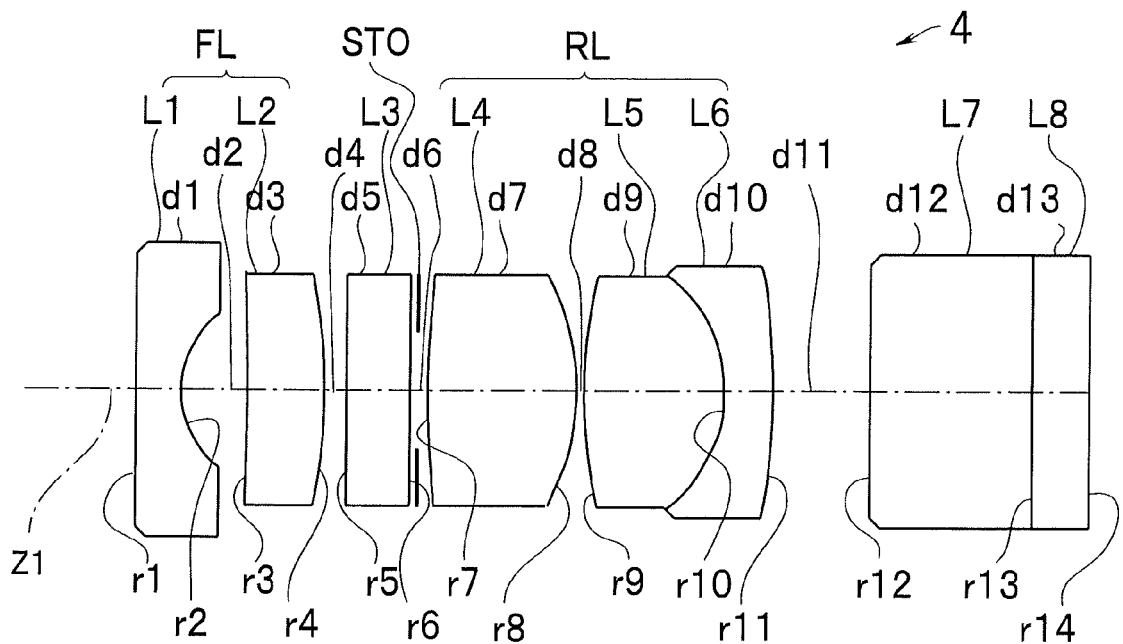
FIG. 4A is a cross-sectional diagram taken along an optical axis for illustrating a lens unit according to example 4.
Figures 4B, 4C, 4D, 4E:
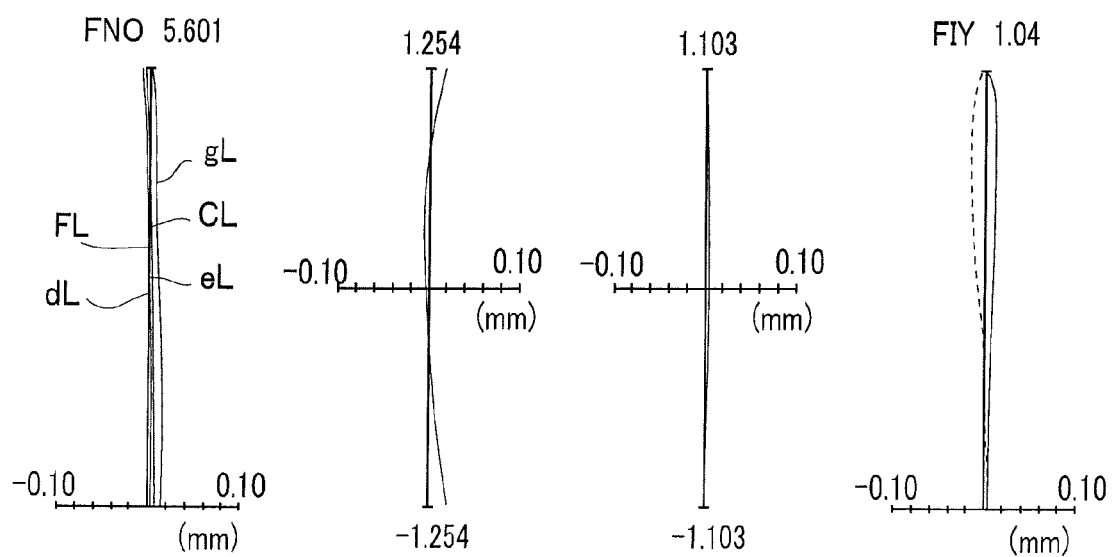
FIG. 4B is a spherical aberration diagram for illustrating the lens unit according to example 4.
FIG. 4C is a coma aberration diagram (M) for illustrating the lens unit according to example 4.
FIG. 4D is a coma aberration diagram (S) for illustrating the lens unit according to example 4.
FIG. 4E is a field curvature diagram for illustrating the lens unit according to example 4.

FNO = 5.601
Focal length of entire unit: f = 1 mm, image height = 1.04 mm, object distance = 10 mm, angle of view = 151.25°
Fr = 1.771 mm,
Ff = −1.276 mm,
fl = −0.986 mm FIG. 4A is a configuration diagram of the lens unit 4 according to the present example, and FIGS. 4B to 4E are aberration diagrams of the lens unit 4.

EXAMPLE 5

Numerical data, etc. of optical members included in a lens unit 5 according to example 5 are indicated below.

TABLE 5

| | | | |
|---|---|---|---|
| r1 = ∞ | d1 = 0.4055 | n1 = 1.88815 | ν1 = 40.76 |
| r2 = 0.8722 | d2 = 0.5855 | n2 = 1.85504 | ν2 = 23.78 |
| r3 = −12.8483 | d3 = 0.6720 | n3 = 1.51564 | ν3 = 75.00 |
| r4 = −3.9869 | d4 = 0.1622 | n4 = 1.83932 | ν4 = 37.16 |
| r5 = ∞ | d5 = 0.5710 | n5 = 1.69979 | ν5 = 55.53 |
| r6 = ∞(STO) | d6 = 0.1614 | n6 = 1.93429 | ν6 = 18.90 |
| r7 = ∞ | d7 = 1.2857 | n7 = 1.51825 | ν7 = 64.14 |
| r8 = −2.014 | d8 = 0.0605 | n8 = 1.61379 | ν8 = 50.20 |
| r9 = 4.3322 | d9 = 1.2613 | | |
| r10 = −1.354 | d10 = 0.4379 | | |

TABLE 5-continued

| | |
|---|---|
| r11 = −5.327 | d11 = 1.0850 |
| r12 = ∞ | d12 = 0.8700 |
| r13 = ∞ | d13 = 0.7368 |
| r14 = ∞ | |

Figure 5A:
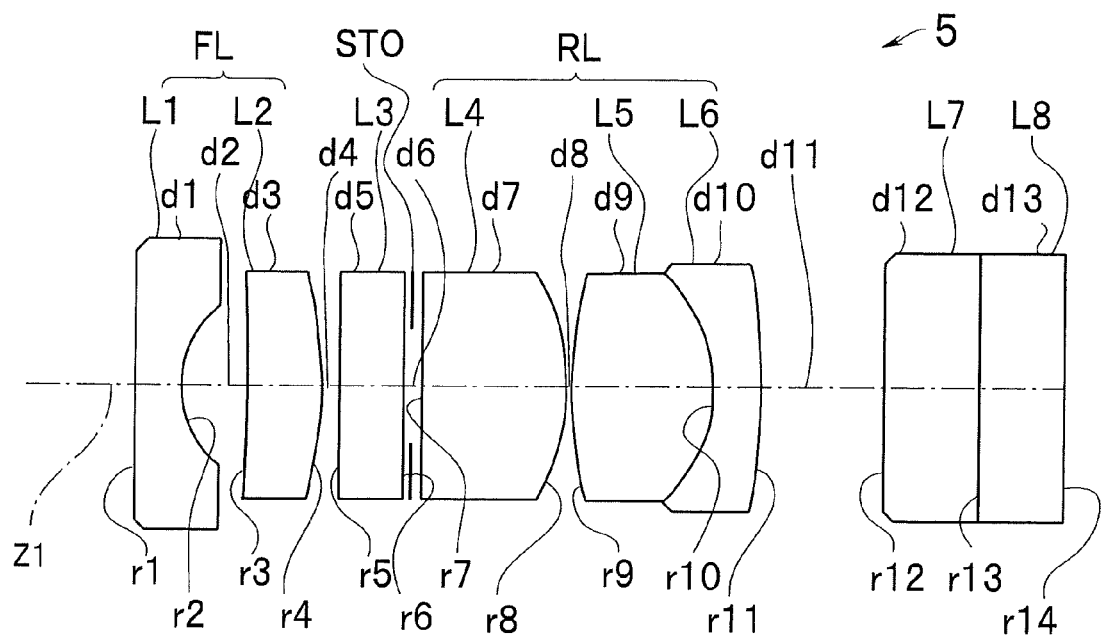
FIG. 5A is a cross-sectional diagram taken along an optical axis for illustrating a lens unit according to example 5.
Figures 5B, 5C, 5D, 5E:
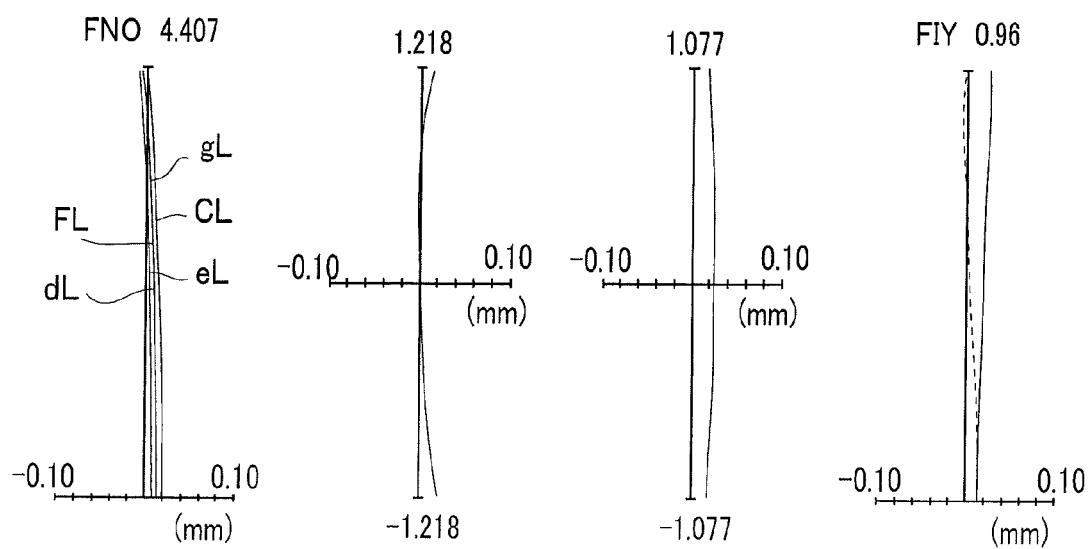
FIG. 5B is a spherical aberration diagram for illustrating the lens unit according to example 5.
FIG. 5C is a coma aberration diagram (M) for illustrating the lens unit according to example 5.
FIG. 5D is a coma aberration diagram (S) for illustrating the lens unit according to example 5.
FIG. 5E is a field curvature diagram for illustrating the lens unit according to example 5.

FNO = 4.407
Focal length of entire unit: f = 1 mm, image height = 0.956 mm, object distance = 11 mm, angle of view = 128.38°
Fr = 1.797 mm,
Ff = −1.439 mm,
fl = −0.982 mm FIG. 5A is a configuration diagram of the lens unit 5 according to the present example, and FIGS. 5B to 5E are aberration diagrams of the lens unit 5.

EXAMPLE 6

Numerical data, etc. of optical members included in a lens unit 6 according to example 6 are indicated below.

TABLE 6

| | | | |
|---|---|---|---|
| r1 = ∞ | d1 = 0.4049 | n1 = 1.88815 | ν1 = 40.76 |
| r2 = 0.9156 | d2 = 0.5512 | n2 = 1.85504 | ν2 = 23.78 |
| r3 = −18.7064 | d3 = 0.6718 | n3 = 1.51564 | ν3 = 75.00 |
| r4 = −7.2381 | d4 = 0.1367 | n4 = 1.83932 | ν4 = 37.16 |
| r5 = ∞ | d5 = 0.5701 | n5 = 1.73234 | ν5 = 54.68 |
| r6 = ∞(STO) | d6 = 0.0302 | n6 = 1.93429 | ν6 = 18.90 |
| r7 = ∞ | d7 = 1.5316 | n7 = 1.51825 | ν7 = 64.14 |
| r8 = −2.061 | d8 = 0.0604 | n8 = 1.61379 | ν8 = 50.20 |
| r9 = 17.9166 | d9 = 1.2833 | | |
| r10 = −1.177 | d10 = 0.4372 | | |
| r11 = −2.6698 | d11 = 1.0074 | | |
| r12 = ∞ | d12 = 1.8234 | | |
| r13 = ∞ | d13 = 0.7356 | | |
| r14 = ∞ | | | |

Figure 6A:
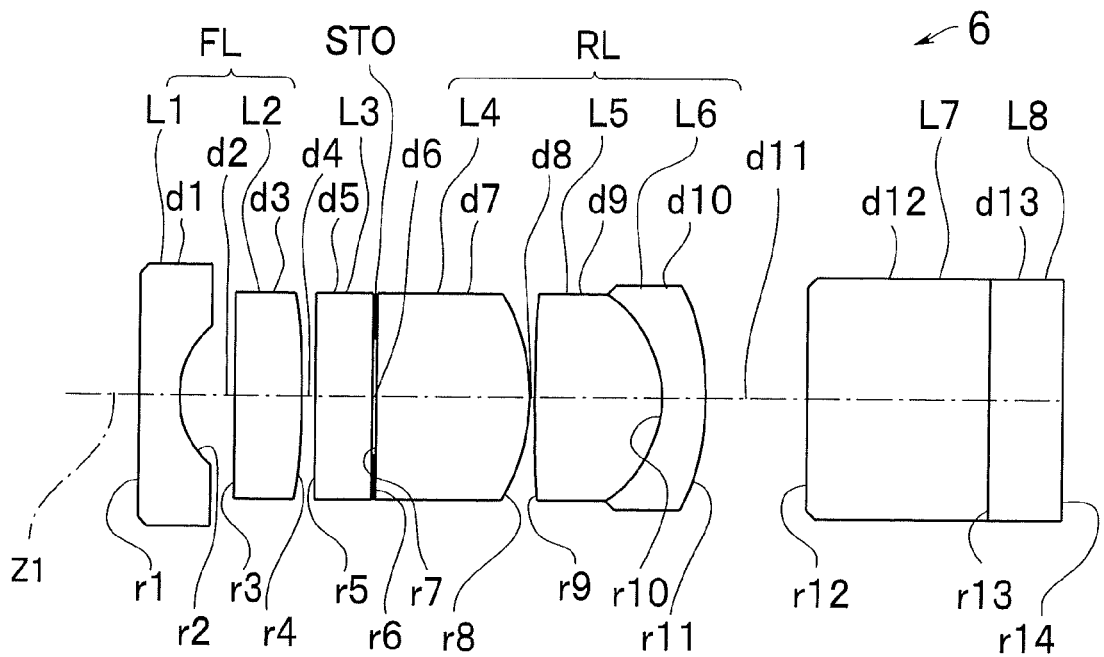
FIG. 6A is a cross-sectional diagram taken along an optical axis for illustrating a lens unit according to example 6.
Figures 6B, 6C, 6D, 6E:
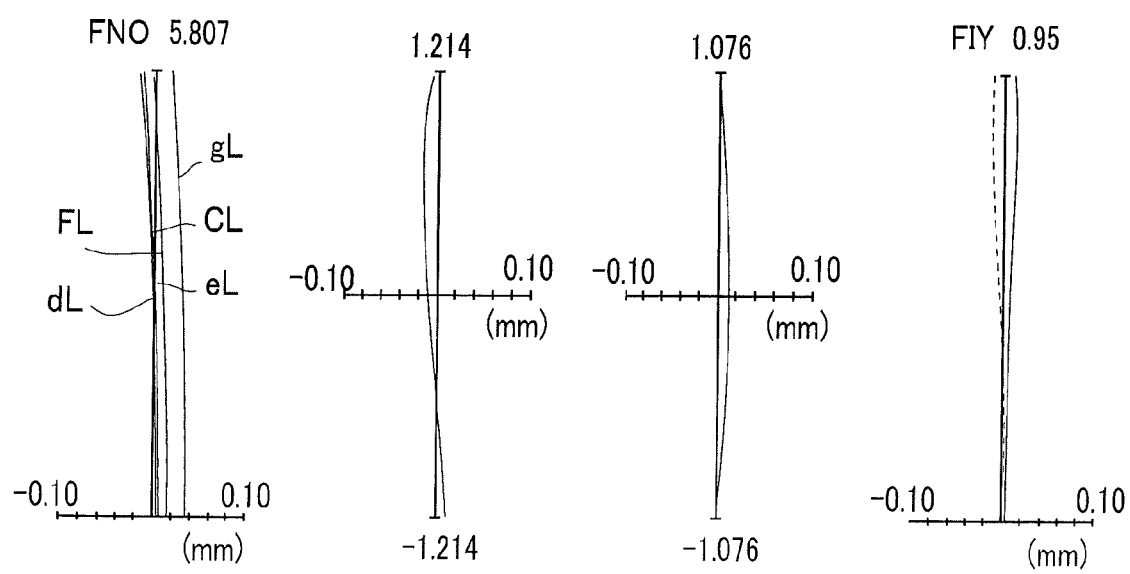
FIG. 6B is a spherical aberration diagram for illustrating the lens unit according to example 6.
FIG. 6C is a coma aberration diagram (M) for illustrating the lens unit according to example 6.
FIG. 6D is a coma aberration diagram (S) for illustrating the lens unit according to example 6.
FIG. 6E is a field curvature diagram for illustrating the lens unit according to example 6.

FNO = 5.807
Focal length of entire unit: f = 1 mm, image height = 0.954 mm, object distance = 10.5 mm, angle of view = 128.1°
Fr = 1.868 mm,
Ff = −1.228 mm,
fl = −1.031 mm FIG. 6A is a configuration diagram of the lens unit 6 according to the present example, and FIGS. 6B to 6E are aberration diagrams of the lens unit 6.

EXAMPLE 7

Numerical data, etc. of optical members included in a lens unit 7 according to example 7 are indicated below.

TABLE 7

| | | | |
|---|---|---|---|
| r1 = ∞ | d1 = 0.4060 | n1 = 1.88815 | ν1 = 40.76 |
| r2 = 0.8641 | d2 = 0.4849 | n2 = 1.85504 | ν2 = 23.78 |
| r3 = −10.1016 | d3 = 0.7113 | n3 = 1.51564 | ν3 = 75.00 |
| r4 = −4.3464 | d4 = 0.0974 | n4 = 1.08642 | ν4 = 34.97 |
| r5 = ∞ | d5 = 0.5716 | n5 = 1.73234 | ν5 = 54.68 |
| r6 = ∞(STO) | d6 = 0.1619 | n6 = 1.93429 | ν6 = 18.90 |
| r7 = 33.7158 | d7 = 1.3665 | n7 = 1.51825 | ν7 = 64.14 |
| r8 = −2.0717 | d8 = 0.0535 | n8 = 1.61379 | ν8 = 50.20 |
| r9 = 9.2024 | d9 = 1.2868 | | |
| r10 = −1.1832 | d10 = 0.4384 | | |
| r11 = −3.0147 | d11 = 1.0102 | | |
| r12 = ∞ | d12 = 1.5354 | | |
| r13 = ∞ | d13 = 0.7376 | | |
| r14 = ∞ | | | |

Figures 7A, 7B, 7C, 7D, 7E:
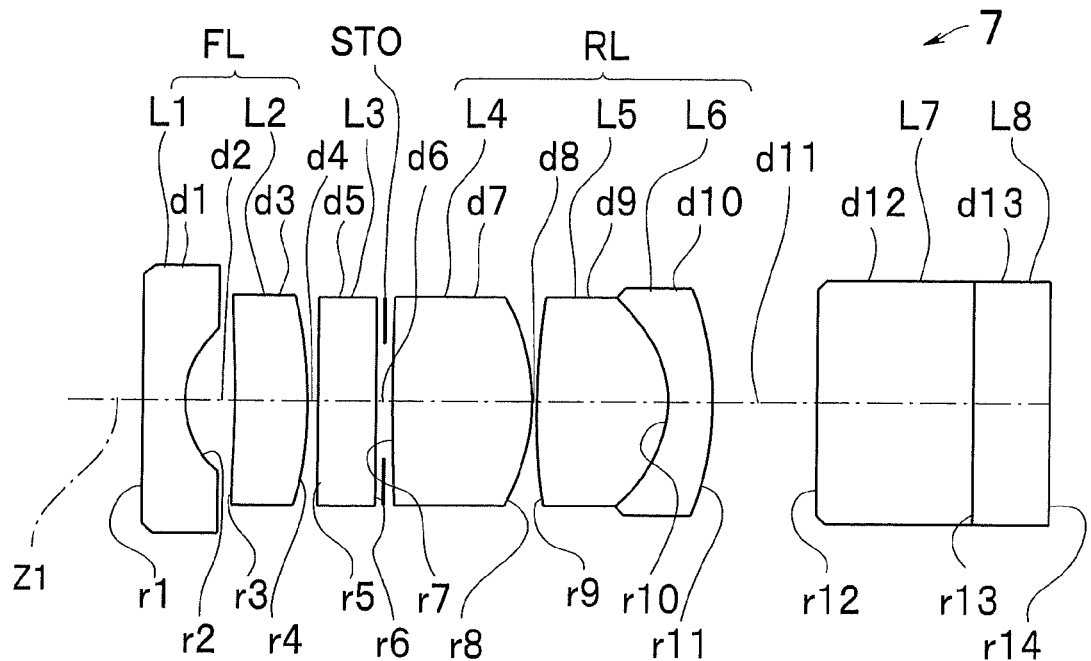
FIG. 7A is a cross-sectional diagram taken along an optical axis for illustrating a lens unit according to example 7.
FIG. 7B is a spherical aberration diagram for illustrating the lens unit according to example 7.
FIG. 7C is a coma aberration diagram (M) for illustrating the lens unit according to example 7.
FIG. 7D is a coma aberration diagram (S) for illustrating the lens unit according to example 7.
FIG. 7E is a field curvature diagram for illustrating the lens unit according to example 7.

FNO = 5.743
Focal length of entire unit: f = 1 mm, image height = 0.957 mm, object distance = 10 mm, angle of view: 127.8°
Fr: 1.853 mm,
Ff = −1.294 mm,
fl = −0.973 mm FIG. 7A is a configuration diagram of the lens unit 7 according to the present example, and FIGS. 7B to 7E are aberration diagrams of the lens unit 7.

EXAMPLE 8

Numerical data, etc. of optical members included in a lens unit 8 according to example 8 are indicated below.

TABLE 8

| | | | |
|---|---|---|---|
| r1 = ∞ | d1 = 0.4056 | n1 = 1.88815 | ν1 = 40.76 |
| r2 = 0.8771 | d2 = 0.4340 | n2 = 1.85504 | ν2 = 23.78 |
| r3 = −10.0931 | d3 = 0.7204 | n3 = 1.51564 | ν3 = 75.00 |
| r4 = −4.1906 | d4 = 0.1258 | n4 = 1.80642 | ν4 = 34.97 |
| r5 = ∞ | d5 = 0.5712 | n5 = 1.73234 | ν5 = 54.68 |
| r6 = ∞(STO) | d6 = 0.1623 | n6 = 1.93429 | ν6 = 18.90 |
| r7 = −50.9076 | d7 = 1.4039 | n7 = 1.51825 | ν7 = 64.14 |
| r8 = −2.0934 | d8 = 0.0707 | n8 = 1.61379 | ν8 = 50.20 |
| r9 = 9.3818 | d9 = 1.2857 | | |
| r10 = −1.1935 | d10 = 0.4381 | | |
| r11 = −2.7935 | d11 = 1.6149 | | |
| r12 = ∞ | d12 = 0.7570 | | |
| r13 = ∞ | d13 = 0.7370 | | |
| r14 = ∞ | | | |

Figure 8A:
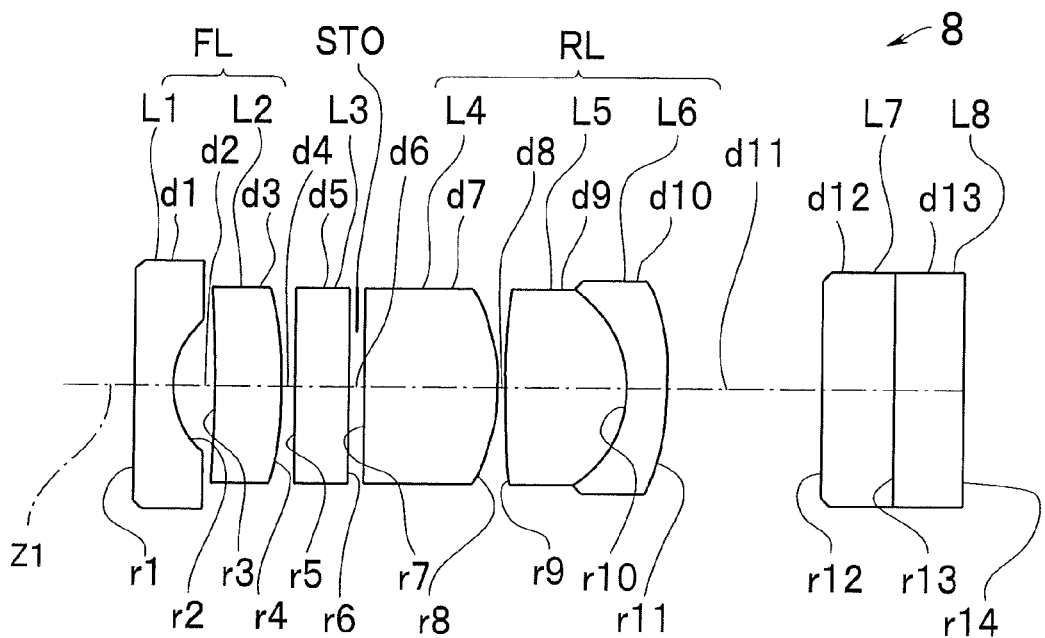
FIG. 8A is a cross-sectional diagram taken along an optical axis for illustrating a lens unit according to example 8.
Figures 8B, 8C, 8D, 8E:
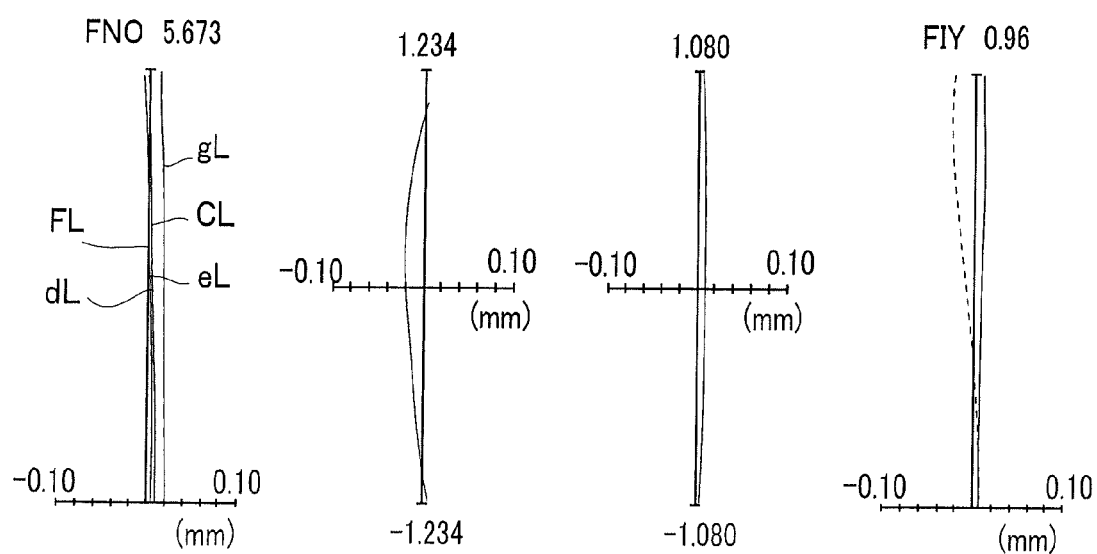
FIG. 8B is a spherical aberration diagram for illustrating the lens unit according to example 8.
FIG. 8C is a coma aberration diagram (M) for illustrating the lens unit according to example 8.
FIG. 8D is a coma aberration diagram (S) for illustrating the lens unit according to example 8.
FIG. 8E is a field curvature diagram for illustrating the lens unit according to example 8.

FNO = 5.673
Focal length of entire unit: f = 1 mm, image height = 0.956 mm, object distance = 10.4 mm, angle of view = 127.98°
Fr = 1.877 mm,
Ff = −1.332 mm,
fl = −0.988 mm FIG. 8A is a configuration diagram of the lens unit 8 according to the present example, and FIGS. 8B to 8E are aberration diagrams of the lens unit 8.

EXAMPLE 9

Numerical data, etc. of optical members included in a lens unit 9 according to example 9 are indicated below.

TABLE 9

| | | | |
|---|---|---|---|
| r1 = ∞ | d1 = 0.4503 | n1 = 1.88815 | ν1 = 40.76 |
| r2 = 0.7879 | d2 = 0.4033 | n2 = 1.85504 | ν2 = 23.78 |
| r3 = ∞ | d3 = 0.8870 | n3 = 1.51564 | ν3 = 75.00 |
| r4 = −18.3149 | d4 = 0.2253 | n4 = 1.88815 | ν4 = 40.76 |
| r5 = ∞ | d5 = 0.5990 | n5 = 1.59143 | ν5 = 61.14 |
| r6 = ∞(STO) | d6 = 0.0544 | n6 = 1.93429 | ν6 = 18.90 |
| r7 = ∞ | d7 = 1.2211 | n7 = 1.51825 | ν7 = 64.14 |
| r8 = −1.8991 | d8 = 0.0901 | n8 = 1.61379 | ν8 = 50.20 |
| r9 = 3.3716 | d9 = 1.0692 | | |
| r10 = −1.6233 | d10 = 0.2600 | | |
| r11 = −5.4907 | d11 = 1.5993 | | |
| r12 = ∞ | d12 = 0.7255 | | |
| r13 = ∞ | d13 = 0.7255 | | |
| r14 = ∞ | | | |

Figure 9A:
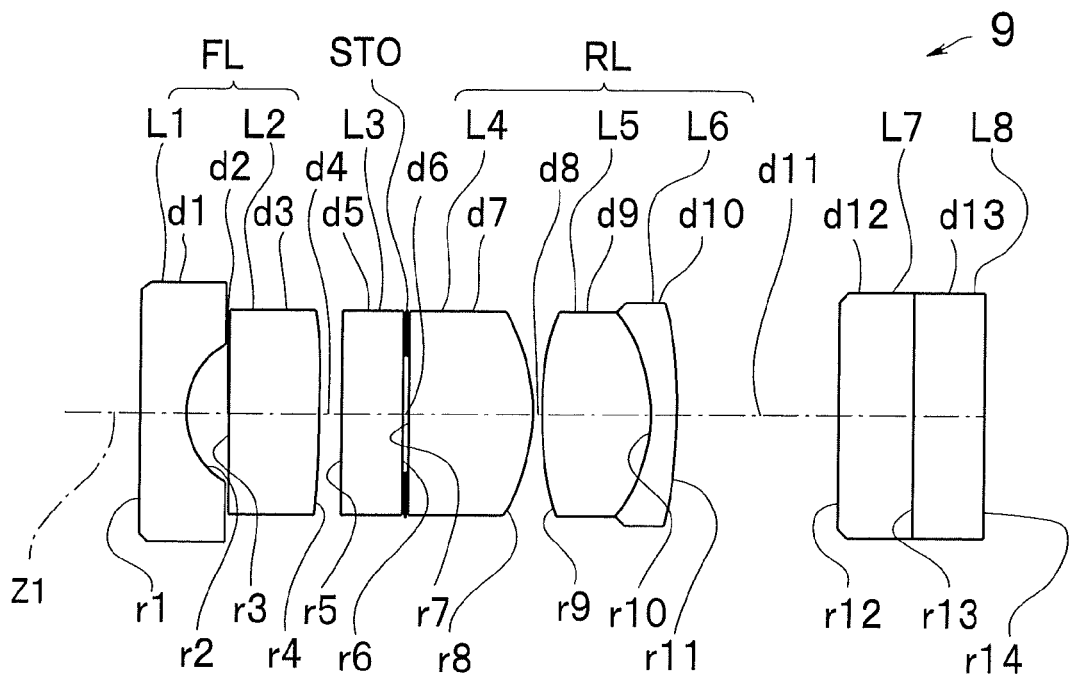
FIG. 9A is a cross-sectional diagram taken along an optical axis for illustrating a lens unit according to example 9.
Figures 9B, 9C, 9D, 9E:
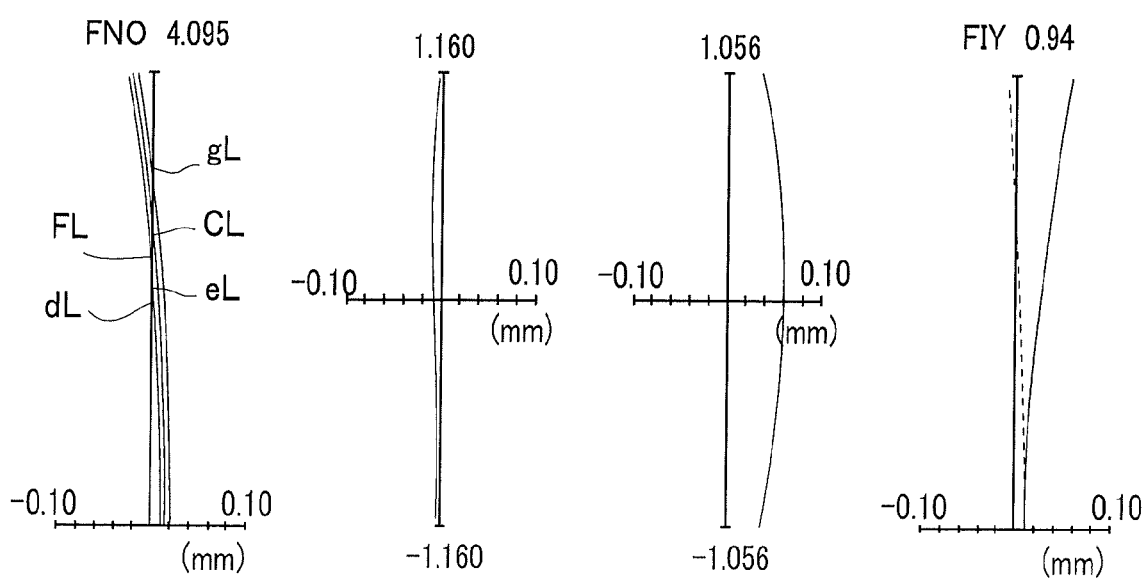
FIG. 9B is a spherical aberration diagram for illustrating the lens unit according to example 9.
FIG. 9C is a coma aberration diagram (M) for illustrating the lens unit according to example 9.
FIG. 9D is a coma aberration diagram (S) for illustrating the lens unit according to example 9.
FIG. 9E is a field curvature diagram for illustrating the lens unit according to example 9.

FNO = 4.095
Focal length of entire unit: f = 1 mm, image height = 0.941 mm, object distance = 18.013 mm, angle of view = 128°
Fr = 1.661 mm,
Ff = −0.967 mm,
fl = −0.887 mm FIG. 9A is a configuration diagram of the lens unit 9 according to the present example, and FIGS. 9B to 9E are aberration diagrams of the lens unit 9.

EXAMPLE 10

Numerical data, etc. of optical members included in a lens unit 10 according to example 10 are indicated below.

TABLE 10

| | | | |
|---|---|---|---|
| r1 = ∞ | d1 = 0.3428 | n1 = 1.88815 | ν1 = 40.76 |
| r2 = 0.8151 | d2 = 0.3428 | n2 = 1.93429 | ν2 = 18.90 |
| r3 = ∞ | d3 = 0.5877 | n3 = 1.88815 | ν3 = 40.76 |
| r4 = −4.3418 | d4 = 0.5526 | n4 = 1.73234 | ν4 = 54.68 |
| r5 = ∞(STO) | d5 = 0.3145 | n5 = 1.93429 | ν5 = 18.90 |
| r6 = −9.0742 | d6 = 0.5507 | n6 = 1.51825 | ν6 = 64.10 |
| r7 = −1.6398 | d7 = 0.0490 | | |
| r8 = 9.8128 | d8 = 0.8160 | | |
| r9 = −1.1151 | d9 = 0.3732 | | |
| r10 = −2.7514 | d10 = 1.6657 | | |
| r11 = ∞ | d11 = 0.9189 | | |
| r12 = ∞ | | | |

Figure 10A:
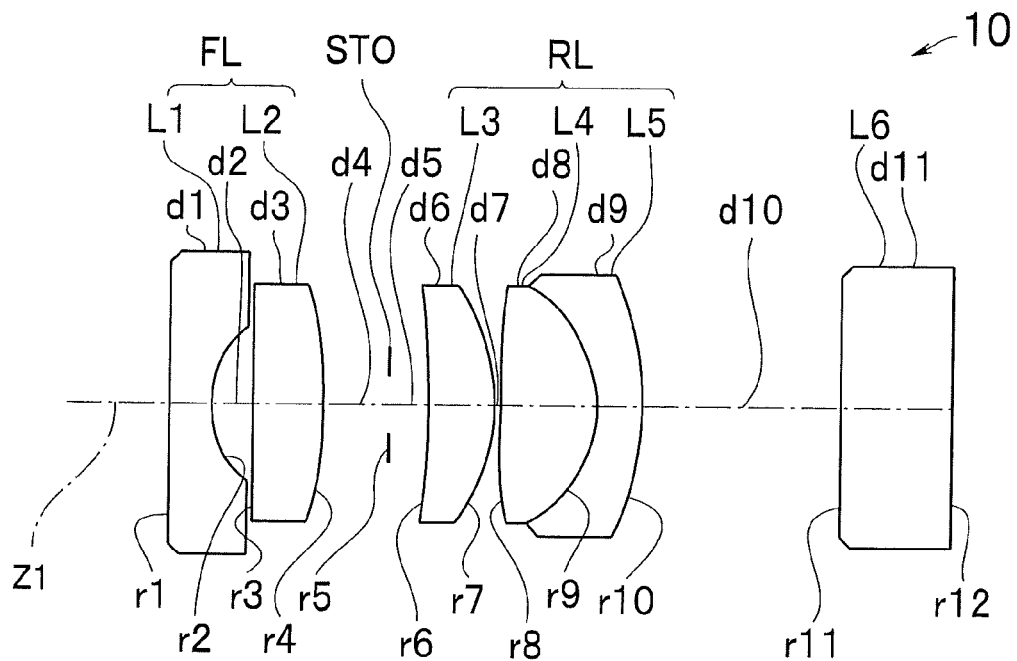
FIG. 10A is a cross-sectional diagram taken along an optical axis for illustrating a lens unit according to example 10.
Figures 10B, 10C, 10D, 10E:
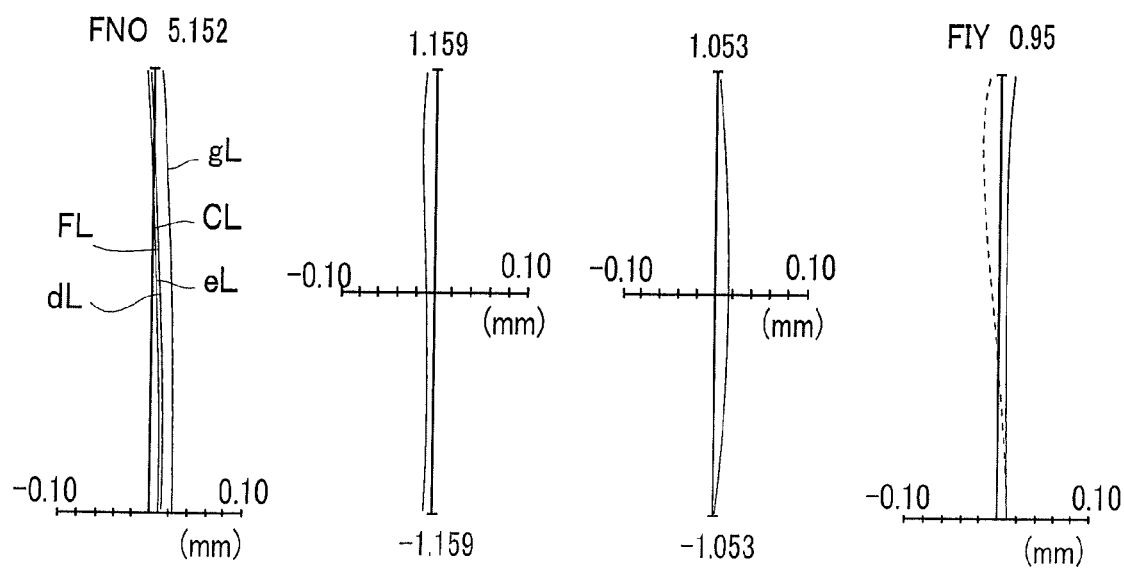
FIG. 10B is a spherical aberration diagram for illustrating the lens unit according to example 10.
FIG. 10C is a coma aberration diagram (M) for illustrating the lens unit according to example 10.
FIG. 10D is a coma aberration diagram (S) for illustrating the lens unit according to example 10.
FIG. 10E is a field curvature diagram for illustrating the lens unit according to example 10.

FNO = 5.152
Focal length of entire unit: f = 1 mm, image height = 0.945 mm, object distance = 19.591 mm, angle of view = 128.18°
Fr = 1.593 mm,
Ff = −1.383 mm,
f1 = −0.918 mm FIG. 10A is a configuration diagram of the lens unit 10 according to the present example, and FIGS. 10B to 10E are aberration diagrams of the lens unit 10.

EXAMPLE 11

Numerical data, etc. of optical members included in a lens unit 11 according to example 11 are indicated below.

TABLE 11

| | | | |
|---|---|---|---|
| r1 = ∞ | d1 = 0.3415 | n1 = 1.88815 | ν1 = 40.76 |
| r2 = 0.8021 | d2 = 0.3415 | n2 = 1.93429 | ν2 = 18.90 |
| r3 = 19.5162 | d3 = 0.5855 | n3 = 1.88815 | ν3 = 40.76 |
| r4 = −5.5767 | d4 = 0.5374 | n4 = 1.73234 | ν4 = 54.68 |
| r5 = ∞(STO) | d5 = 0.3008 | n5 = 1.93429 | ν5 = 18.90 |
| r6 = −10.1204 | d6 = 0.5486 | n6 = 1.51825 | ν6 = 64.10 |
| r7 = −1.6388 | d7 = 0.0488 | | |
| r8 = 9.33 | d8 = 0.8161 | | |
| r9 = −1.1122 | d9 = 0.3718 | | |
| r10 = −2.746 | d10 = 1.6684 | | |
| r11 = ∞ | d11 = 0.9154 | | |
| r12 = ∞ | | | |

Figure 11A:
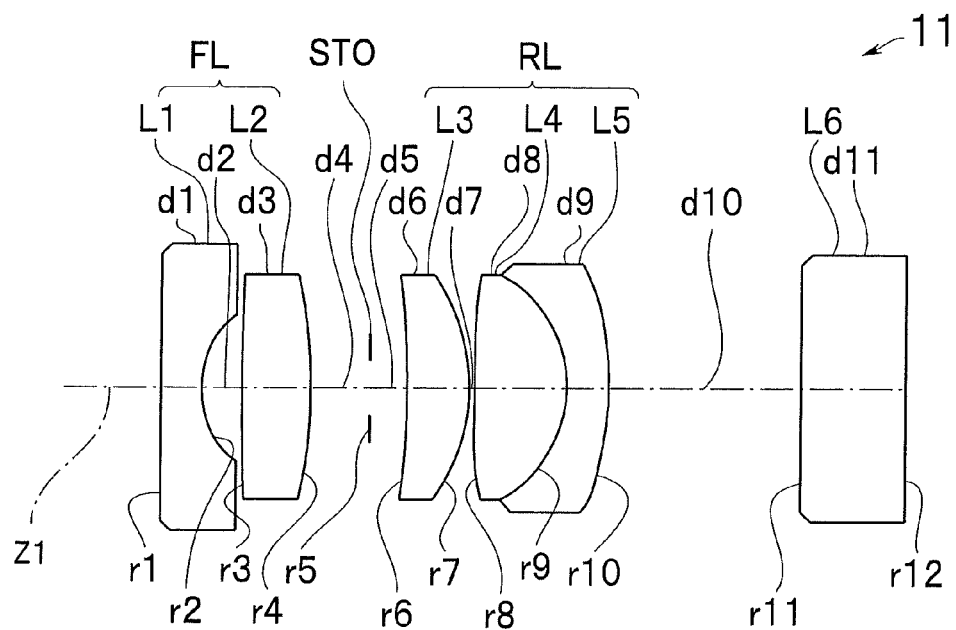
FIG. 11A is a cross-sectional diagram taken along an optical axis for illustrating a lens unit according to example 11.
Figures 11B, 11C, 11D, 11E:
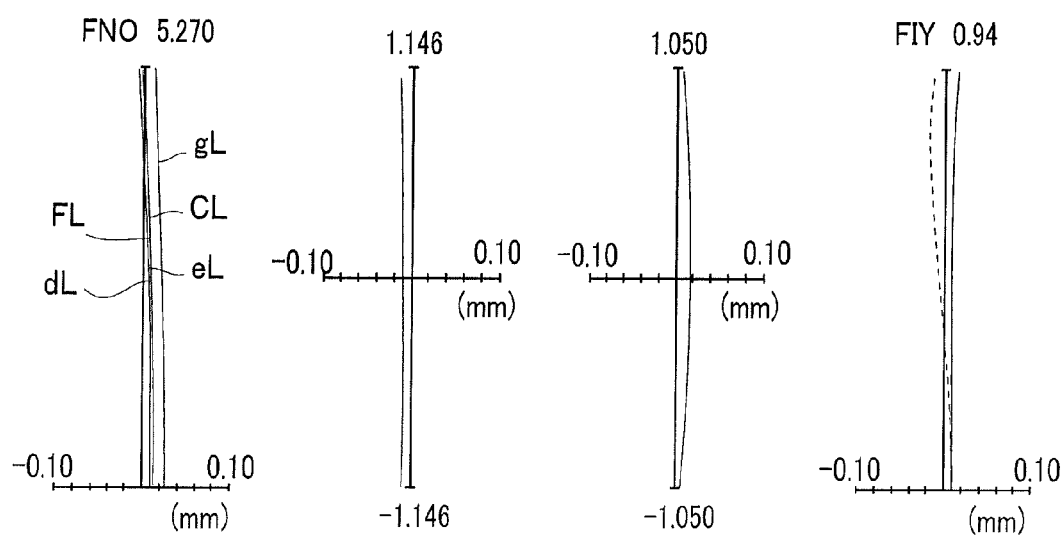
FIG. 11B is a spherical aberration diagram for illustrating the lens unit according to example 11.
FIG. 11C is a coma aberration diagram (M) for illustrating the lens unit according to example 11.
FIG. 11D is a coma aberration diagram (S) for illustrating the lens unit according to example 11.
FIG. 11E is a field curvature diagram for illustrating the lens unit according to example 11.

FNO = 5.27
Focal length of entire unit: f = 1 mm, image height = 0.942 mm, object distance = 19.516 mm, angle of view = 128.19°
Fr = 1.567 mm,
Ff = −1.320 mm,
f1 = −0.903 mm FIG. 11A is a configuration diagram of the lens unit 11 according to the present example, and FIGS. 11B to 11E are aberration diagrams of the lens unit 11.

EXAMPLE 12

Numerical data, etc. of optical members included in a lens unit 12 according to example 12 are indicated below.

TABLE 12

| | | | |
|---|---|---|---|
| r1 = ∞ | d1 = 0.4500 | n1 = 1.88815 | ν1 = 40.76 |
| r2 = 0.8070 | d2 = 0.4179 | n2 = 1.93429 | ν2 = 18.90 |
| r3 = ∞ | d3 = 0.7529 | n3 = 1.51564 | ν3 = 75.00 |
| r4 = −18.8614 | d4 = 0.1692 | n4 = 1.88815 | ν4 = 40.76 |
| r5 = ∞ | d5 = 0.5632 | n5 = 1.73234 | ν5 = 54.68 |
| r6 = ∞(STO) | d6 = 0.0545 | n6 = 1.93429 | ν6 = 18.90 |
| r7 = ∞ | d7 = 1.1960 | n7 = 1.51825 | ν7 = 64.14 |
| r8 = −1.8960 | d8 = 0.1058 | n8 = 1.61379 | ν8 = 50.20 |
| r9 = 6.3884 | d9 = 1.1373 | | |
| r10 = −1.3424 | d10 = 0.4320 | | |
| r11 = −3.9951 | d11 = 1.5444 | | |
| r12 = ∞ | d12 = 0.7300 | | |

TABLE 12-continued

| | |
|---|---|
| r13 = ∞ | d13 = 0.7500 |
| r14 = ∞ | |

Figure 12A:
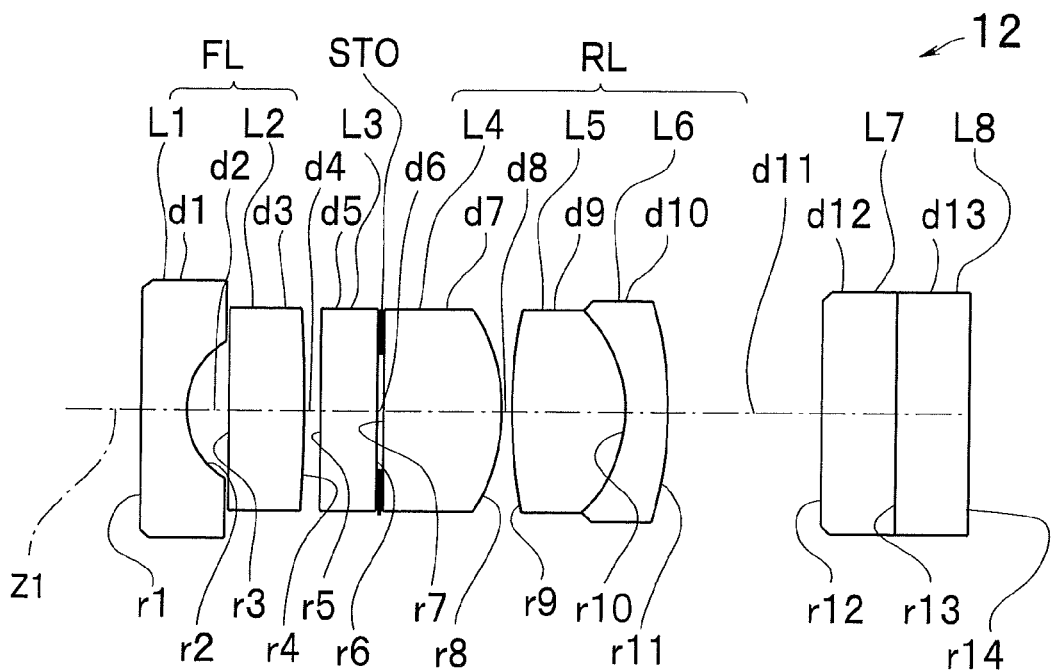
FIG. 12A is a cross-sectional diagram taken along an optical axis for illustrating a lens unit according to example 12.
Figures 12B, 12C, 12D, 12E:
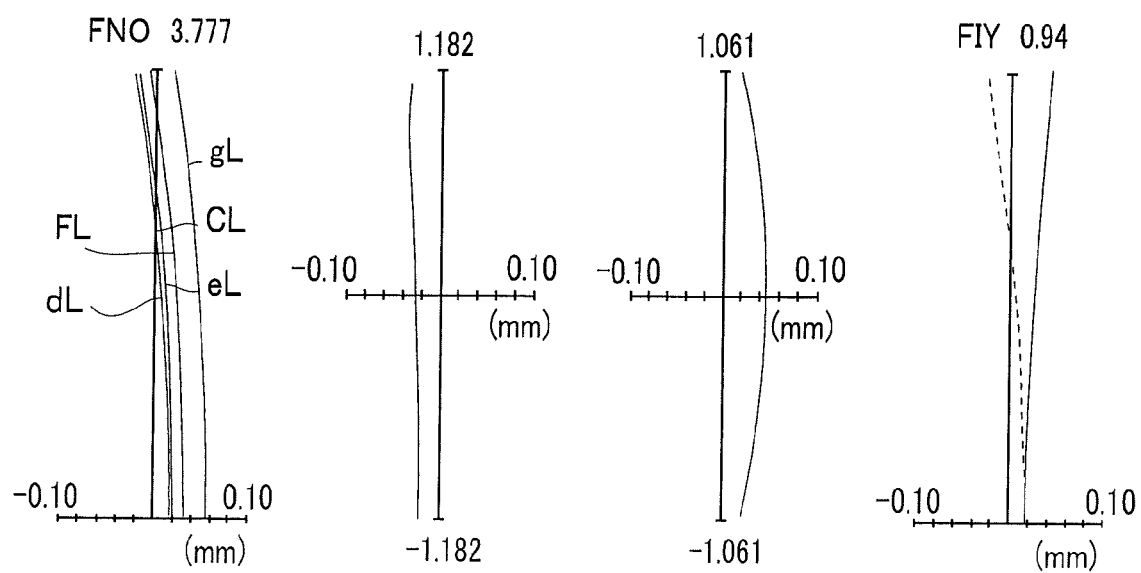
FIG. 12B is a spherical aberration diagram for illustrating the lens unit according to example 12.
FIG. 12C is a coma aberration diagram (M) for illustrating the lens unit according to example 12.
FIG. 12D is a coma aberration diagram (S) for illustrating the lens unit according to example 12.
FIG. 12E is a field curvature diagram for illustrating the lens unit according to example 12.

FNO = 3.777
Focal length of entire unit: f = 1 mm, image height = 0.943 mm, object distance = 16 mm, angle of view = 127.83°
Fr = 1.668 mm,
Ff = −0.993 mm,
f7 = −0.909 mm FIG. 12A is a configuration diagram of the lens unit 12 according to the present example, and FIGS. 12B to 12E are aberration diagrams of the lens unit 12.

EXAMPLE 13

Numerical data, etc. of optical members included in a lens unit 13 according to example 13 are indicated below.

TABLE 13

| | | | |
|---|---|---|---|
| r1 = ∞ | d1 = 0.4000 | n1 = 1.88815 | ν1 = 40.76 |
| r2 = 0.8406 | d2 = 0.6160 | n2 = 1.85504 | ν2 = 23.78 |
| r3 = −5.8882 | d3 = 0.7945 | n3 = 1.51564 | ν3 = 75.00 |
| r4 = −3.9255 | d4 = 0.2866 | n4 = 1.83932 | ν4 = 37.16 |
| r5 = ∞ | d5 = 0.5627 | n5 = 1.59143 | ν5 = 61.14 |
| r6 = ∞(STO) | d6 = 0.1599 | n6 = 1.93429 | ν6 = 18.90 |
| r7 = 11.8394 | d7 = 1.3354 | n7 = 1.51825 | ν7 = 64.14 |
| r8 = −2.1677 | d8 = 0.0527 | | |
| r9 = 3.4717 | d9 = 1.1636 | | |
| r10 = −1.4365 | d10 = 0.4316 | | |
| r11 = −6.1946 | d11 = 1.0000 | | |
| r12 = ∞ | d12 = 2.0100 | | |
| r13 = ∞ | | | |

Figure 13A:
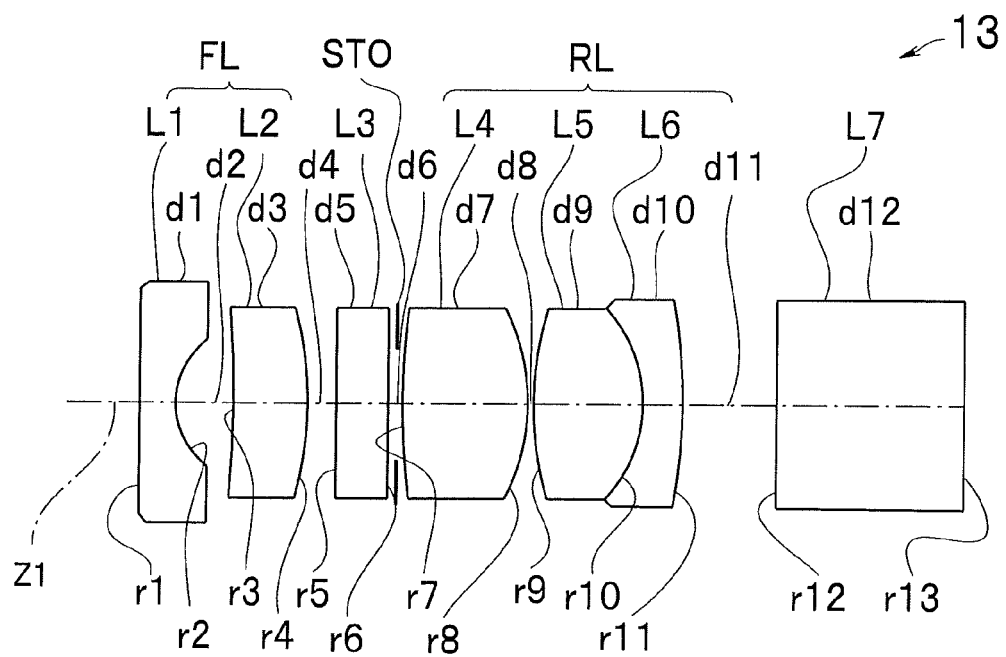
FIG. 13A is a cross-sectional diagram taken along an optical axis for illustrating a lens unit according to example 13.
Figures 13B, 13C, 13D, 13E:
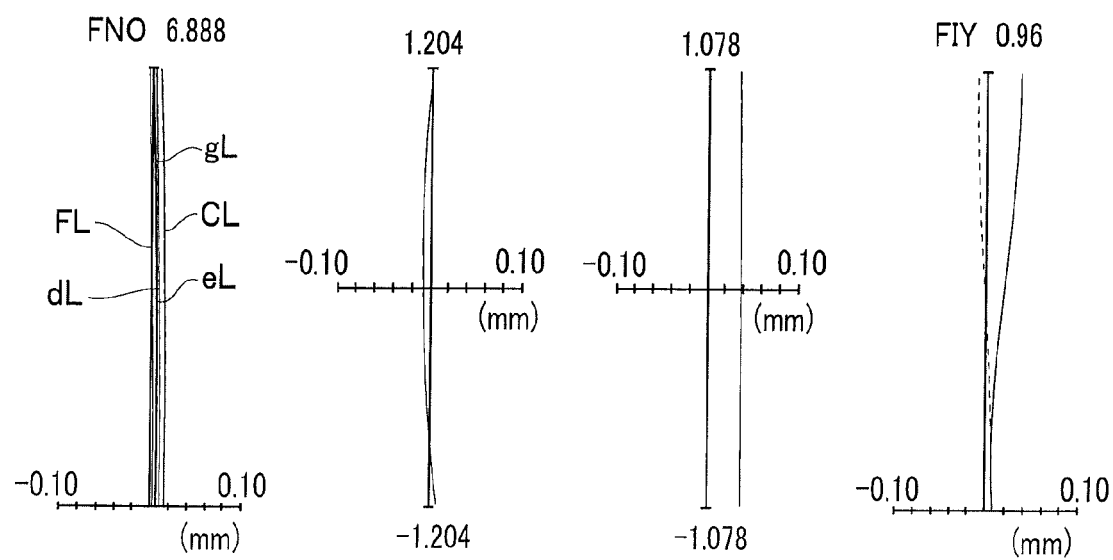
FIG. 13B is a spherical aberration diagram for illustrating the lens unit according to example 13.
FIG. 13C is a coma aberration diagram (M) for illustrating the lens unit according to example 13.
FIG. 13D is a coma aberration diagram (S) for illustrating the lens unit according to example 13.
FIG. 13E is a field curvature diagram for illustrating the lens unit according to example 13.

FNO = 6.888
Focal length of entire unit: f = 1 mm, image height = 0.96 mm, object distance = 9.8 mm, angle of view = 129.73°
Fr = 1.863 mm,
Ff = −1.226 mm,
f1 = −0.946 mm FIG. 13A is a configuration diagram of the lens unit 13 according to the present example, and FIGS. 13B to 13E are aberration diagrams of the lens unit 13.

EXAMPLE 14

Numerical data, etc. of optical members included in a lens unit 14 according to example 14 are indicated below. A material of a first lens L1 of each of lens units 14 to 25 is yttria-stabilized zirconia (YSZ).

TABLE 14

| | | | |
|---|---|---|---|
| r1 = ∞ | d1 = 0.5433 | n1 = 2.18246 | ν1 = 33.01 |
| r2 = 0.9685 | d2 = 0.4165 | n2 = 1.93429 | ν2 = 18.90 |
| r3 = ∞ | d3 = 0.7243 | n3 = 1.51564 | ν3 = 75.00 |
| r4 = −5.4012 | d4 = 0.1449 | n4 = 1.88815 | ν4 = 40.76 |
| r5 = ∞ | d5 = 0.5614 | n5 = 1.73234 | ν5 = 54.68 |
| r6 = ∞(STO) | d6 = 0.0543 | n6 = 1.93429 | ν6 = 18.90 |
| r7 = ∞ | d7 = 1.5375 | n7 = 1.51825 | ν7 = 64.14 |
| r8 = −2.181 | d8 = 0.1992 | n8 = 1.61379 | ν8 = 50.20 |
| r9 = 5.1839 | d9 = 1.1770 | | |
| r10 = −1.3201 | d10 = 0.4305 | | |
| r11 = −4.2501 | d11 = 1.5232 | | |
| r12 = ∞ | d12 = 0.7600 | | |
| r13 = ∞ | d13 = 0.7243 | | |
| r14 = ∞ | | | |

Figure 14A:
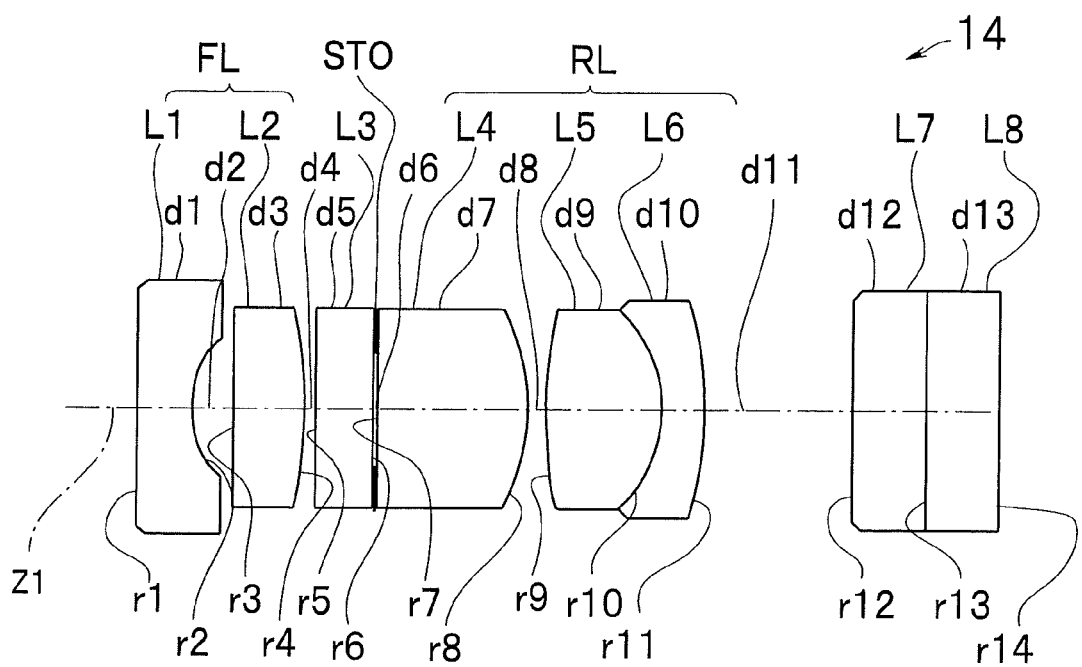
FIG. 14A is a cross-sectional diagram taken along an optical axis for illustrating a lens unit according to example 14.
Figures 14B, 14C, 14D, 14E:
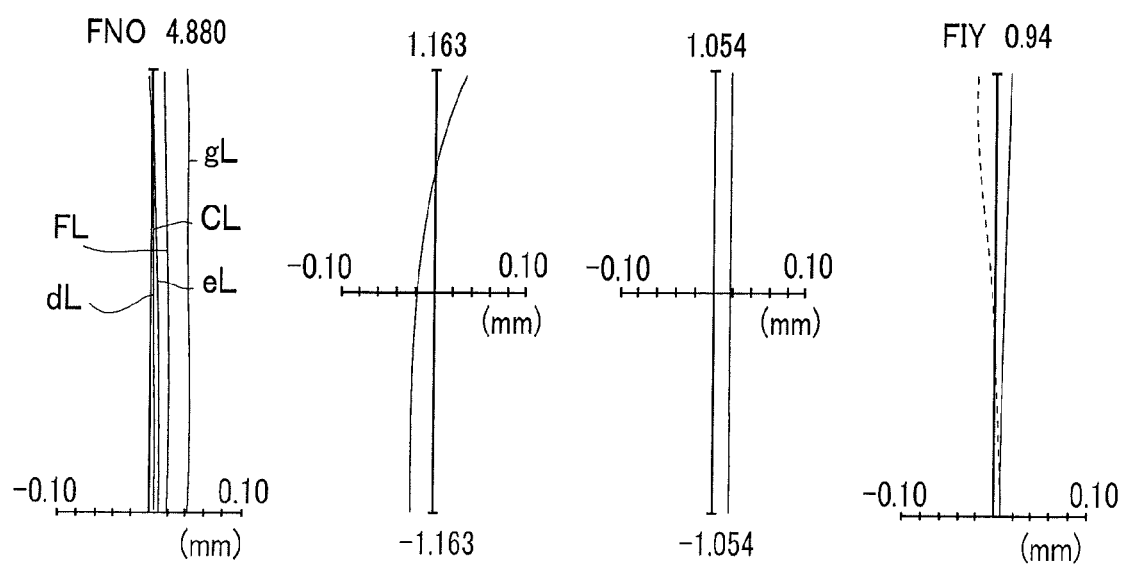
FIG. 14B is a spherical aberration diagram for illustrating the lens unit according to example 14.
FIG. 14C is a coma aberration diagram (M) for illustrating the lens unit according to example 14.
FIG. 14D is a coma aberration diagram (S) for illustrating the lens unit according to example 14.
FIG. 14E is a field curvature diagram for illustrating the lens unit according to example 14.

FNO = 4.88
Focal length of entire unit: f = 1 mm, image height = 0.94 mm, object distance = 18.108 mm, angle of view = 127.62°
Fr = 1.812 mm,
Ff = −1.135 mm,
f1 = −0.819 mm FIG. 14A is a configuration diagram of the lens unit 14 according to the present example, and FIGS. 14B to 14E are aberration diagrams of the lens unit 14.

EXAMPLE 15

Numerical data, etc. of optical members included in a lens unit 15 according to example 15 are indicated below.

TABLE 15

| | | | |
|---|---|---|---|
| r1 = ∞ | d1 = 0.5440 | n1 = 2.18246 | v1 = 33.01 |
| r2 = 0.9605 | d2 = 0.4171 | n2 = 1.93429 | v2 = 18.90 |
| r3 = ∞ | d3 = 0.7253 | n3 = 1.51564 | v3 = 75.00 |
| r4 = −4.8664 | d4 = 0.1451 | n4 = 1.88815 | v4 = 40.76 |
| r5 = ∞ | d5 = 0.5621 | n5 = 1.73234 | v5 = 54.68 |
| r6 = ∞(STO) | d6 = 0.0544 | n6 = 1.93429 | v6 = 18.90 |
| r7 = ∞ | d7 = 1.5159 | n7 = 1.51825 | v7 = 64.14 |
| r8 = −2.1868 | d8 = 0.1993 | n8 = 1.61379 | v8 = 50.20 |
| r9 = 5.9359 | d9 = 1.1787 | | |
| r10 = −1.3219 | d10 = 0.4311 | | |
| r11 = −3.8915 | d11 = 1.5247 | | |
| r12 = ∞ | d12 = 0.7510 | | |
| r13 = ∞ | d13 = 0.7253 | | |
| r14 = ∞ | | | |

Figure 15A:
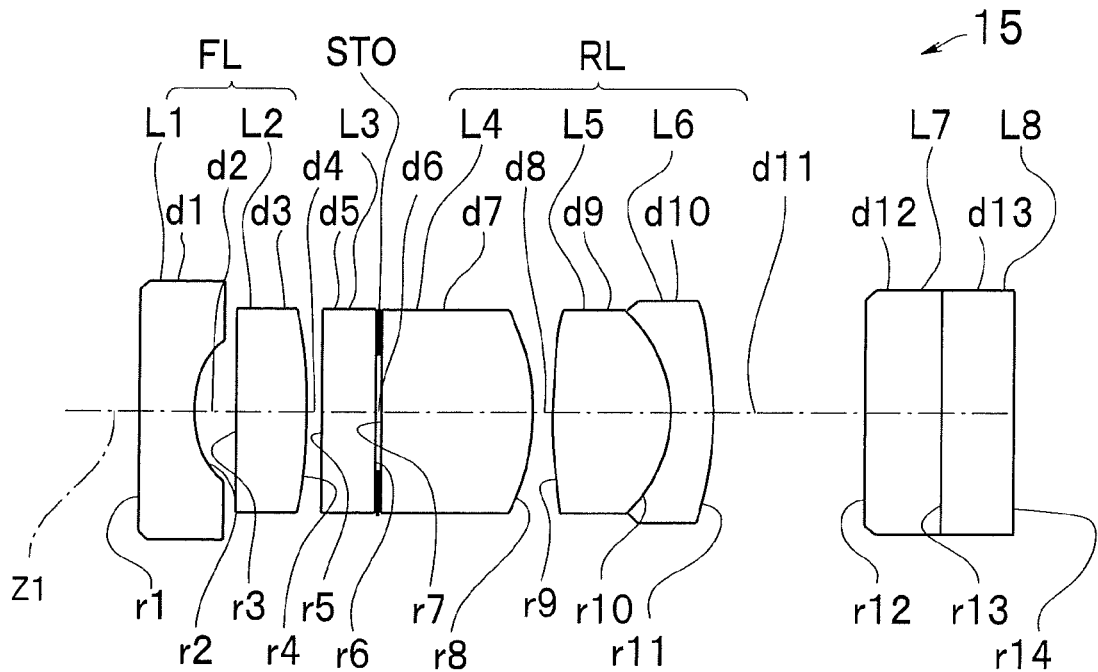
FIG. 15A is a cross-sectional diagram taken along an optical axis for illustrating a lens unit according to example 15.
Figures 15B, 15C, 15D, 15E:
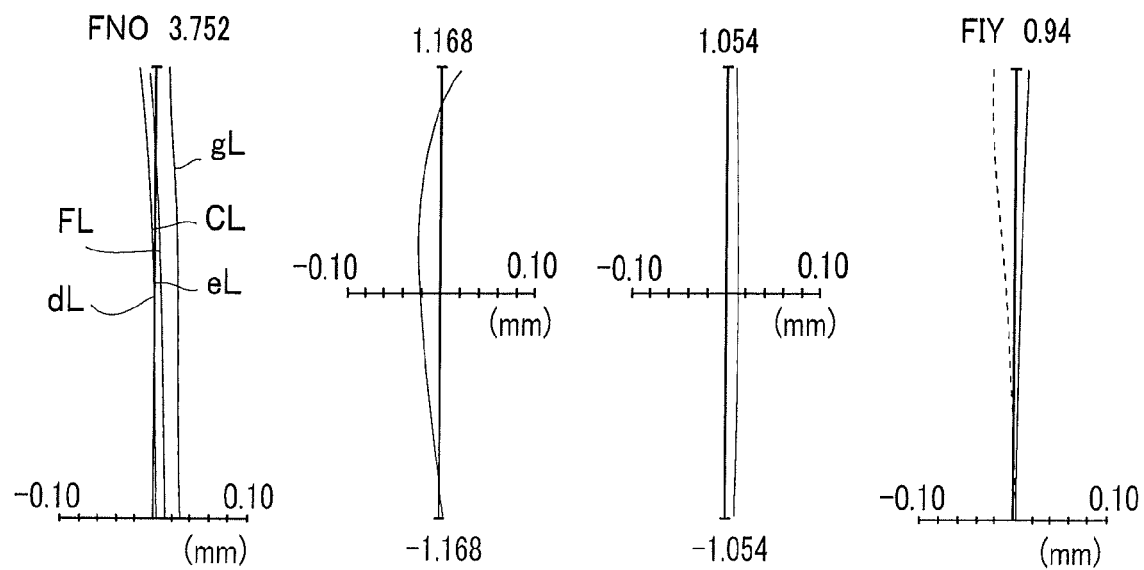
FIG. 15B is a spherical aberration diagram for illustrating the lens unit according to example 15.
FIG. 15C is a coma aberration diagram (M) for illustrating the lens unit according to example 15.
FIG. 15D is a coma aberration diagram (S) for illustrating the lens unit according to example 15.
FIG. 15E is a field curvature diagram for illustrating the lens unit according to example 15.

FNO = 3.752
Focal length of entire unit: f = 1 mm, image height = 0.941 mm, object distance = 18.134 mm, angle of view = 127.85°
Fr = 1.832 mm,
Ff = −1.174 mm,
fl = −0.812 mm FIG. 15A is a configuration diagram of the lens unit 15 according to the present example, and FIGS. 15B to 15E are aberration diagrams of the lens unit 15.

EXAMPLE 16

Numerical data, etc. of optical members included in a lens unit 16 according to example 16 are indicated below.

TABLE 16

| | | | |
|---|---|---|---|
| r1 = ∞ | d1 = 0.5435 | n1 = 2.18246 | v1 = 33.01 |
| r2 = 0.9913 | d2 = 0.6042 | n2 = 1.93429 | v2 = 18.90 |
| r3 = ∞ | d3 = 0.7247 | n3 = 1.51564 | v3 = 75.00 |
| r4 = −4.7185 | d4 = 0.1449 | n4 = 1.88815 | v4 = 40.76 |
| r5 = ∞ | d5 = 0.5617 | n5 = 1.73234 | v5 = 54.68 |
| r6 = ∞(STO) | d6 = 0.0544 | n6 = 1.93429 | v6 = 18.90 |
| r7 = ∞ | d7 = 1.4653 | n7 = 1.51825 | v7 = 64.14 |
| r8 = −2.3106 | d8 = 0.1992 | n8 = 1.61379 | v8 = 50.20 |
| r9 = 6.1978 | d9 = 1.1777 | | |
| r10 = −1.3208 | d10 = 0.4308 | | |
| r11 = −4.093 | d11 = 1.5433 | | |
| r12 = ∞ | d12 = 0.7498 | | |
| r13 = ∞ | d13 = 0.7247 | | |
| r14 = ∞ | | | |

Figure 16A:
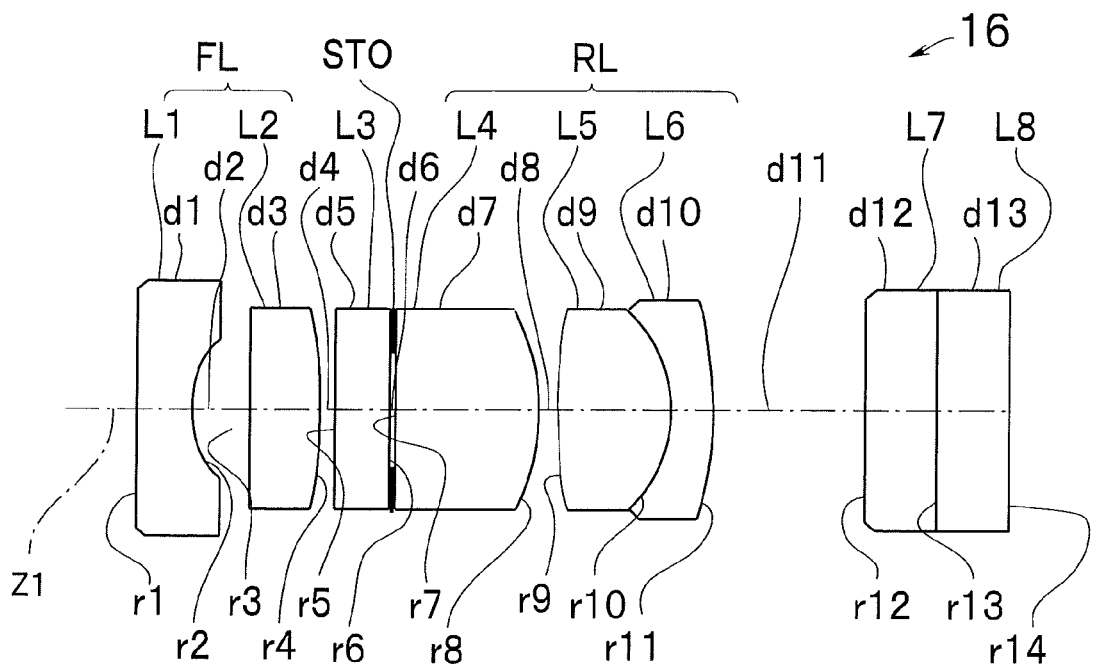
FIG. 16A is a cross-sectional diagram taken along an optical axis for illustrating a lens unit according to example 16.
Figures 16B, 16C, 16D, 16E:
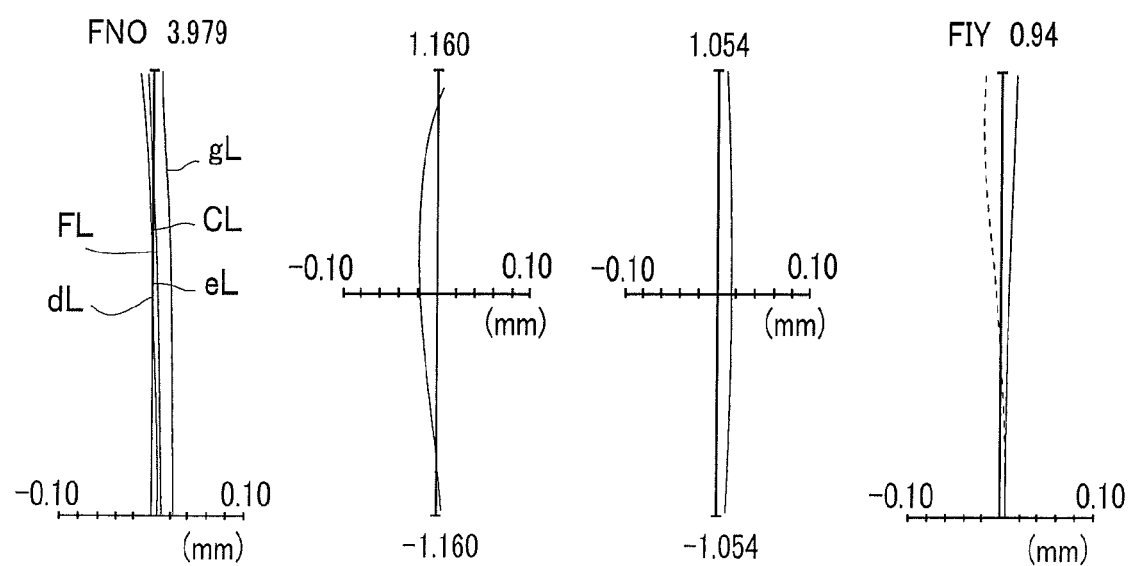
FIG. 16B is a spherical aberration diagram for illustrating the lens unit according to example 16.
FIG. 16C is a coma aberration diagram (M) for illustrating the lens unit according to example 16.
FIG. 16D is a coma aberration diagram (S) for illustrating the lens unit according to example 16.
FIG. 16E is a field curvature diagram for illustrating the lens unit according to example 16.

FNO = 3.979
Focal length of entire unit: f = 1 mm, image height = 0.94 mm, object distance = 18.118 mm, angle of view = 127.81°
Fr = 1.933 mm,
Ff = −1.310 mm,
fl = −0.838 mm FIG. 16A is a configuration diagram of the lens unit 16 according to the present example, and FIGS. 16B to 16E are aberration diagrams of the lens unit 16.

EXAMPLE 17

Numerical data, etc. of optical members included in a lens unit 17 according to example 17 are indicated below.

TABLE 17

| | | | |
|---|---|---|---|
| r1 = ∞ | d1 = 0.4500 | n1 = 2.18246 | v1 = 33.01 |
| r2 = 1.0405 | d2 = 0.4448 | n2 = 1.93429 | v2 = 18.90 |
| r3 = ∞ | d3 = 0.8448 | n3 = 1.51564 | v3 = 75.00 |
| r4 = −7.461 | d4 = 0.1978 | n4 = 1.80642 | v4 = 34.97 |
| r5 = ∞ | d5 = 0.5584 | n5 = 1.73234 | v5 = 54.68 |
| r6 = ∞(STO) | d6 = 0.0540 | n6 = 1.93429 | v6 = 18.90 |
| r7 = ∞ | d7 = 1.7385 | n7 = 1.51825 | v7 = 64.14 |
| r8 = −2.3919 | d8 = 0.1101 | n8 = 1.61379 | v8 = 50.20 |
| r9 = 6.4097 | d9 = 1.1708 | | |
| r10 = −1.3886 | d10 = 0.4282 | | |
| r11 = −3.4605 | d11 = 1.2423 | | |
| r12 = ∞ | d12 = 1.8883 | | |
| r13 = ∞ | d13 = 0.7300 | | |
| r14 = ∞ | | | |

Figure 17A:
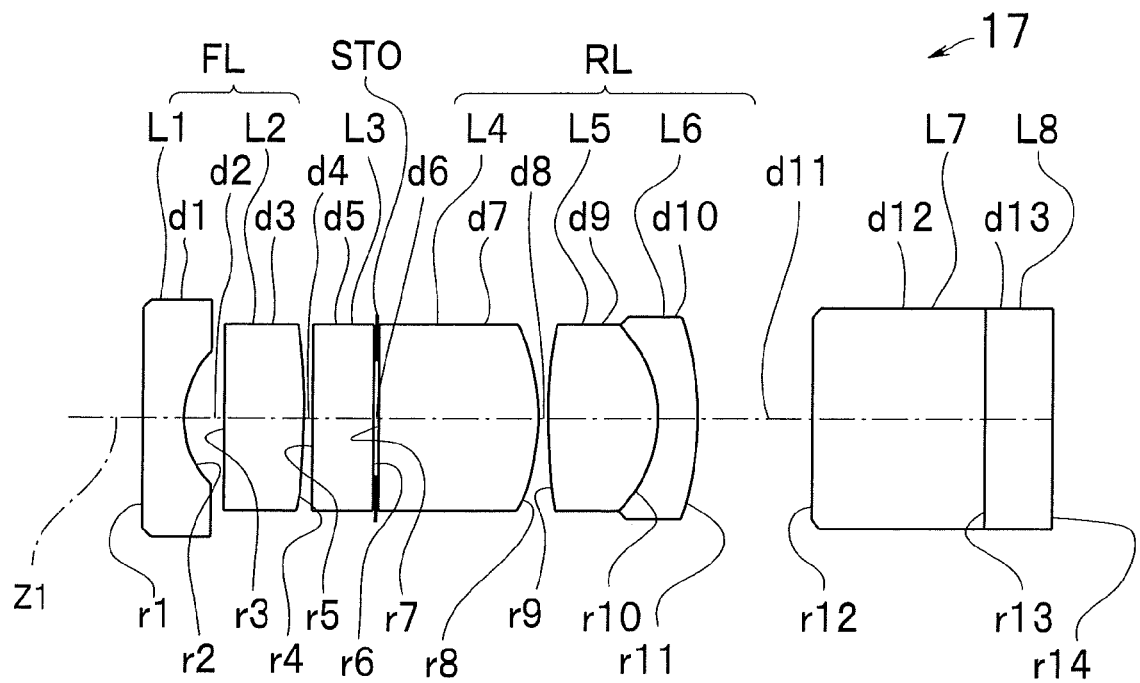
FIG. 17A is a cross-sectional diagram taken along an optical axis for illustrating a lens unit according to example 17.
Figures 17B, 17C, 17D, 17E:
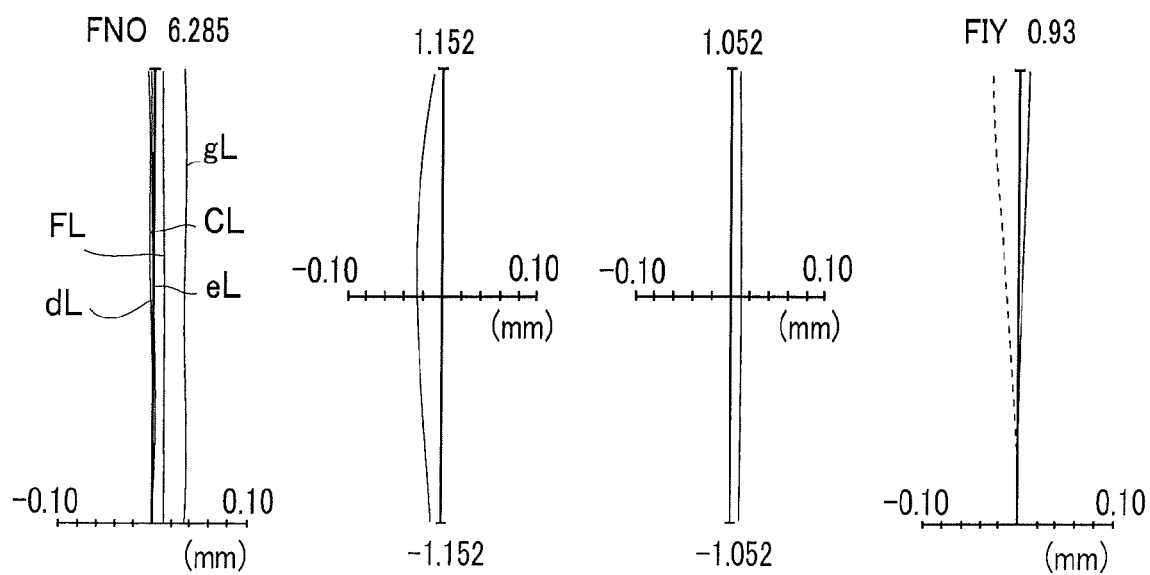
FIG. 17B is a spherical aberration diagram for illustrating the lens unit according to example 17.
FIG. 17C is a coma aberration diagram (M) for illustrating the lens unit according to example 17.
FIG. 17D is a coma aberration diagram (S) for illustrating the lens unit according to example 17.
FIG. 17E is a field curvature diagram for illustrating the lens unit according to example 17.

FNO = 6.285
Focal length of entire unit: f = 1 mm, image height = 0.935 mm, object distance = 17.89 mm, angle of view = 127.85°
Fr = 1.967 mm,
Ff = −1.290 mm,
fl = −0.880 mm FIG. 17A is a configuration diagram of the lens unit 17 according to the present example, and FIGS. 17B to 17E are aberration diagrams of the lens unit 17.

EXAMPLE 18

Numerical data, etc. of optical members included in a lens unit 18 according to example 18 are indicated below.

TABLE 18

| | | | |
|---|---|---|---|
| r1 = ∞ | d1 = 0.4483 | n1 = 2.18246 | v1 = 33.01 |
| r2 = 1.0038 | d2 = 0.3786 | n2 = 1.93429 | v2 = 18.90 |
| r3 = ∞ | d3 = 0.9165 | n3 = 1.51564 | v3 = 75.00 |
| r4 = −6.1690 | d4 = 0.3261 | n4 = 1.83932 | v4 = 37.16 |
| r5 = ∞ | d5 = 0.5597 | n5 = 1.73234 | v5 = 54.68 |
| r6 = ∞(STO) | d6 = 0.0542 | n6 = 1.93429 | v6 = 18.90 |
| r7 = ∞ | d7 = 1.2616 | n7 = 1.51825 | v7 = 64.14 |
| r8 = −2.2838 | d8 = 0.2388 | n8 = 1.61379 | v8 = 50.20 |
| r9 = 6.9881 | d9 = 1.1735 | | |
| r10 = −1.3162 | d10 = 0.4293 | | |
| r11 = −3.2867 | d11 = 1.7932 | | |
| r12 = ∞ | d12 = 0.7422 | | |
| r13 = ∞ | d13 = 0.7222 | | |
| r14 = ∞ | | | |

Figure 18A:
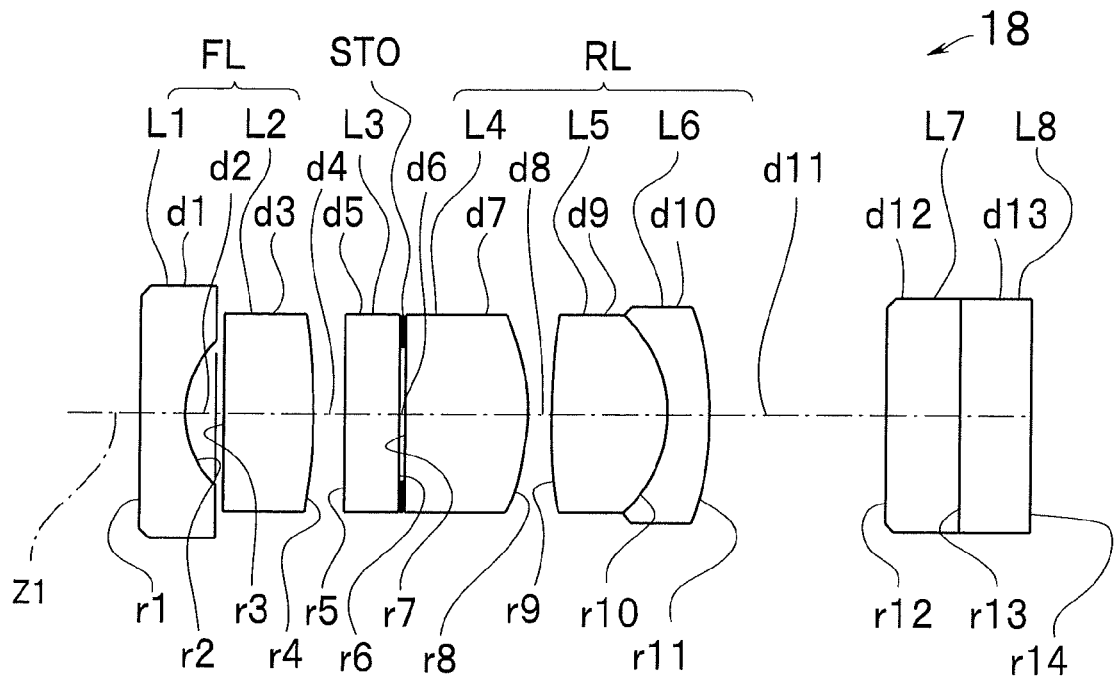
FIG. 18A is a cross-sectional diagram taken along an optical axis for illustrating a lens unit according to example 18.
Figures 18B, 18C, 18D, 18E:
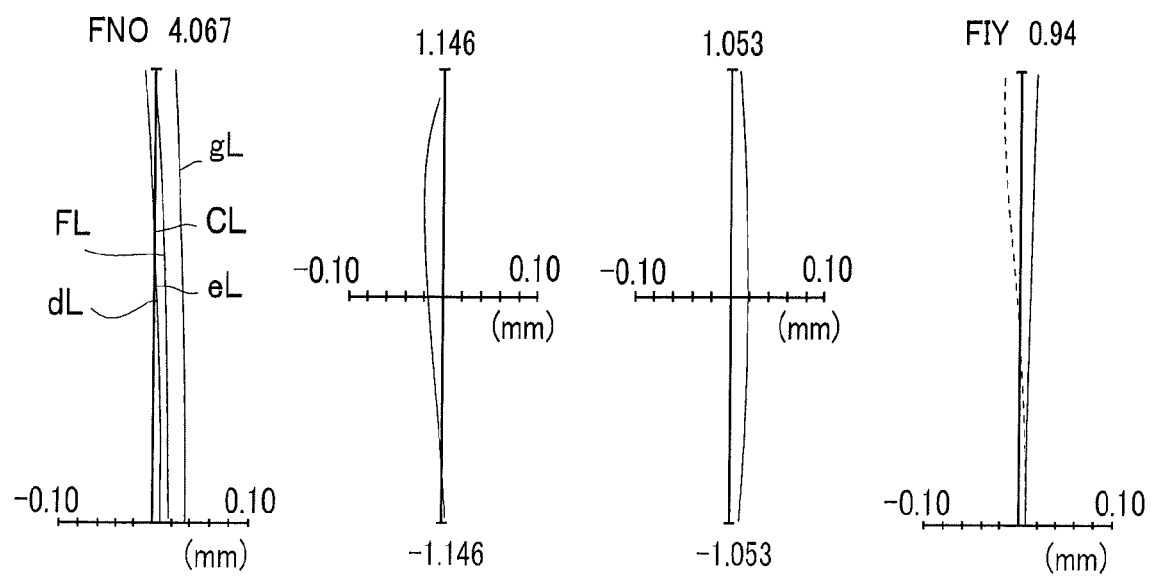
FIG. 18B is a spherical aberration diagram for illustrating the lens unit according to example 18.
FIG. 18C is a coma aberration diagram (M) for illustrating the lens unit according to example 18.
FIG. 18D is a coma aberration diagram (S) for illustrating the lens unit according to example 18.
FIG. 18E is a field curvature diagram for illustrating the lens unit according to example 18.

FNO = 4.067
Focal length of entire unit: f = 1 mm, image height = 0.937 mm, object distance = 17.932 mm, angle of view = 127.96°
Fr = 1.931 mm,
Ff = −1.144 mm,
fl = −0.849 mm FIG. 18A is a configuration diagram of the lens unit 18 according to the present example, and FIGS. 18B to 18E are aberration diagrams of the lens unit 18.

EXAMPLE 19

Numerical data, etc. of optical members included in a lens unit 19 according to example 19 are indicated below.

TABLE 19

| | | | |
|---|---|---|---|
| r1 = ∞ | d1 = 0.5000 | n1 = 2.18246 | v1 = 33.01 |
| r2 = 0.9456 | d2 = 0.4142 | n2 = 1.93429 | v2 = 18.90 |
| r3 = ∞ | d3 = 0.7204 | n3 = 1.51564 | v3 = 75.00 |
| r4 = −7.4010 | d4 = 0.3945 | n4 = 2.18246 | v4 = 33.01 |
| r5 = ∞ | d5 = 0.5583 | n5 = 1.73234 | v5 = 54.68 |
| r6 = ∞(STO) | d6 = 0.2341 | n6 = 1.93429 | v6 = 18.90 |
| r7 = 15.5855 | d7 = 1.2410 | n7 = 1.51825 | v7 = 64.14 |
| r8 = −2.6460 | d8 = 0.1987 | n8 = 1.61379 | v8 = 50.20 |
| r9 = 6.2845 | d9 = 1.1706 | | |
| r10 = −1.3129 | d10 = 0.4282 | | |

TABLE 19-continued

| | |
|---|---|
| r11 = −8.7654 | d11 = 1.4404 |
| r12 = ∞ | d12 = 0.7600 |
| r13 = ∞ | d13 = 0.7000 |
| r14 = ∞ | |

Figure 19A:
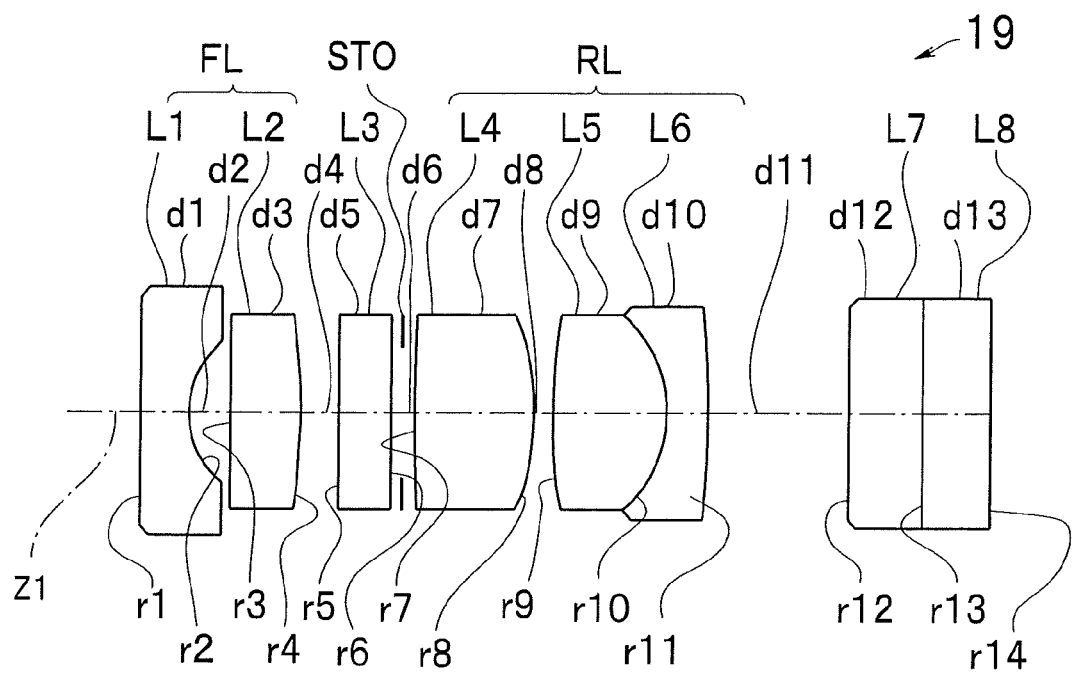
FIG. 19A is a cross-sectional diagram taken along an optical axis for illustrating a lens unit according to example 19.
Figures 19B, 19C, 19D, 19E:
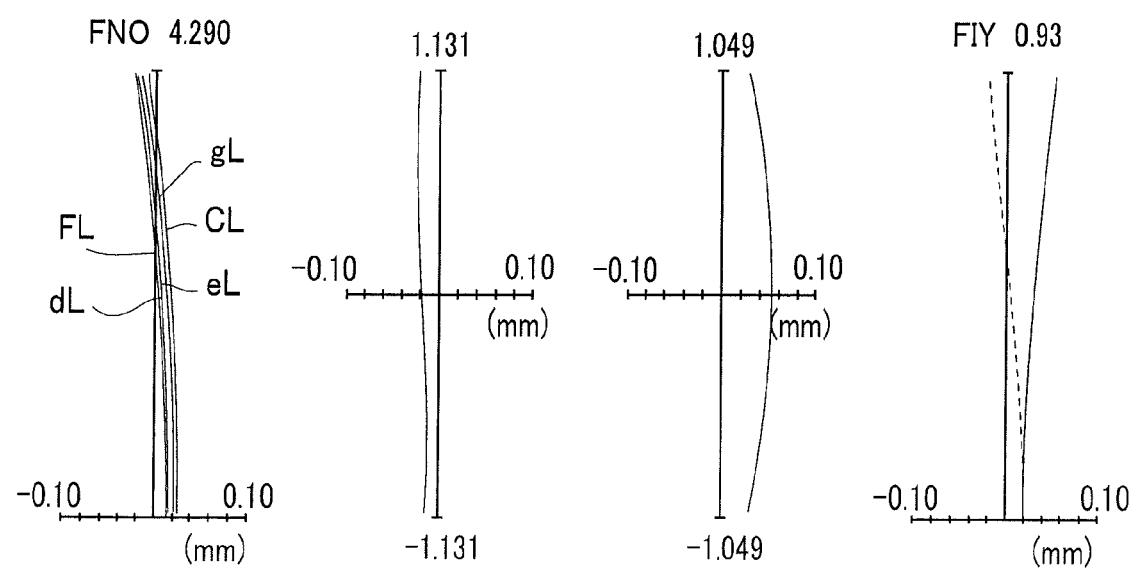
FIG. 19B is a spherical aberration diagram for illustrating the lens unit according to example 19.
FIG. 19C is a coma aberration diagram (M) for illustrating the lens unit according to example 19.
FIG. 19D is a coma aberration diagram (S) for illustrating the lens unit according to example 19.
FIG. 19E is a field curvature diagram for illustrating the lens unit according to example 19.

FNO = 4.29
Focal length of entire unit: f = 1 mm, image height = 0.935 mm, object distance = 18 mm, angle of view = 127.93°
Fr = 1.756 mm,
Ff = −1.000 mm,
fl = −0.800 mm FIG. 19A is a configuration diagram of the lens unit 19 according to the present example, and FIGS. 19B to 19E are aberration diagrams of the lens unit 19.

EXAMPLE 20

Numerical data, etc. of optical members included in a lens unit 20 according to example 20 are indicated below.

TABLE 20

| | | | |
|---|---|---|---|
| r1 = ∞ | d1 = 0.5000 | n1 = 2.18246 | ν1 = 33.01 |
| r2 = 0.9247 | d2 = 0.5971 | n2 = 1.93429 | ν2 = 18.90 |
| r3 = ∞ | d3 = 0.7238 | n3 = 1.51564 | ν3 = 75.00 |
| r4 = −4.4671 | d4 = 0.1448 | n4 = 1.88815 | ν4 = 40.76 |
| r5 = ∞ | d5 = 0.5609 | n5 = 1.73234 | ν5 = 54.68 |
| r6 = ∞(STO) | d6 = 0.0543 | n6 = 1.93429 | ν6 = 18.90 |
| r7 = ∞ | d7 = 1.2470 | n7 = 1.51825 | ν7 = 64.14 |
| r8 = −2.0417 | d8 = 0.1990 | n8 = 1.61379 | ν8 = 50.20 |
| r9 = 4.9784 | d9 = 1.1761 | | |
| r10 = −1.3191 | d10 = 0.4302 | | |
| r11 = −6.7685 | d11 = 1.3457 | | |
| r12 = ∞ | d12 = 0.7500 | | |
| r13 = ∞ | d13 = 0.7238 | | |
| r14 = ∞ | | | |

Figure 20A:
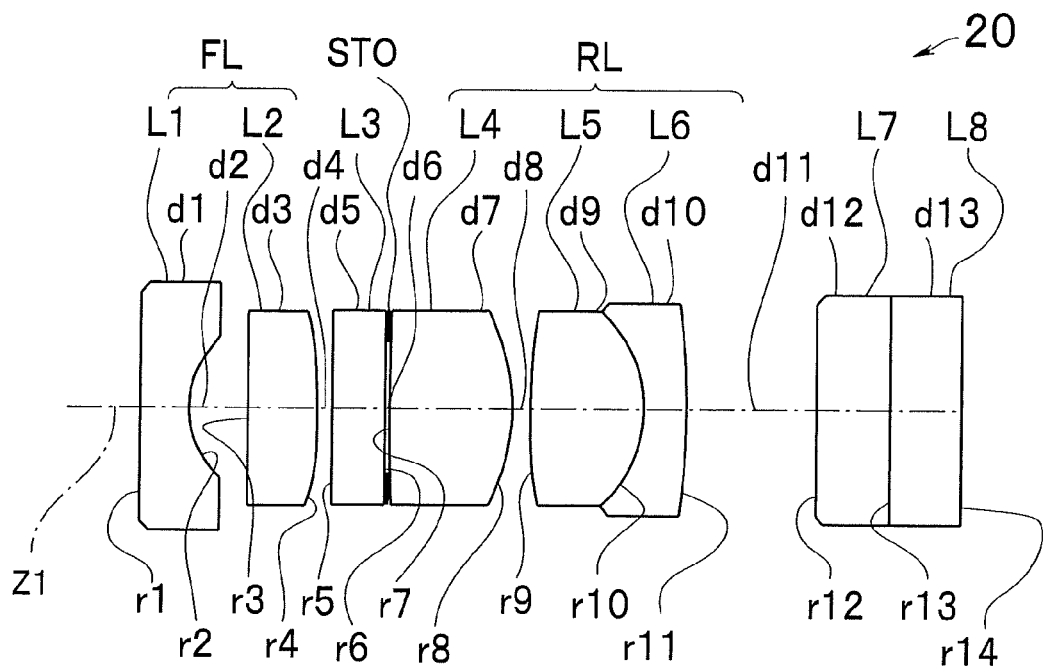
FIG. 20A is a cross-sectional diagram taken along an optical axis for illustrating a lens unit according to example 20.
Figures 20B, 20C, 20D, 20E:
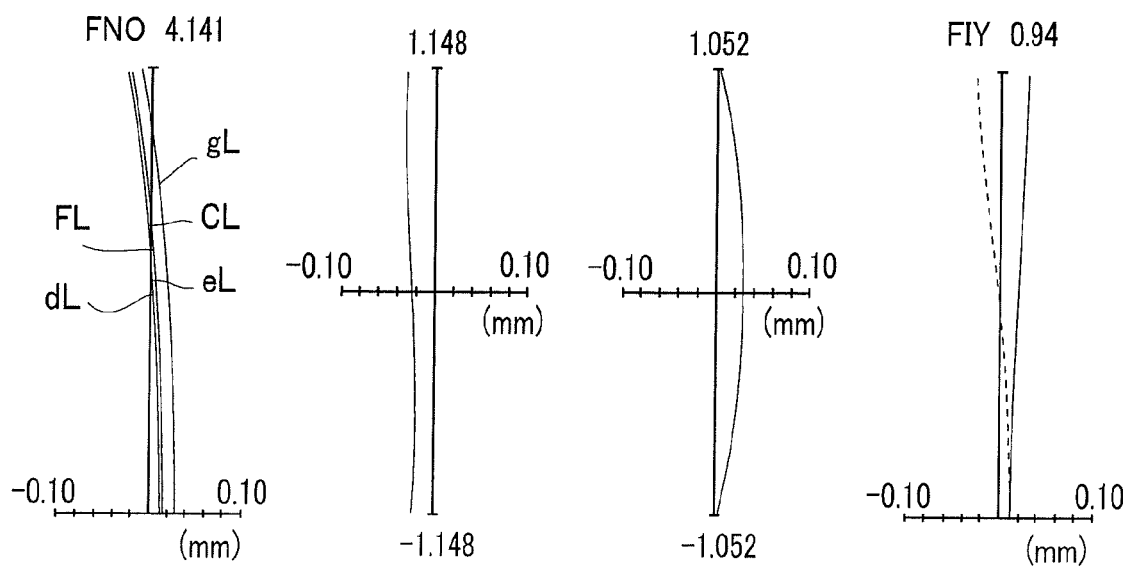
FIG. 20B is a spherical aberration diagram for illustrating the lens unit according to example 20.
FIG. 20C is a coma aberration diagram (M) for illustrating the lens unit according to example 20.
FIG. 20D is a coma aberration diagram (S) for illustrating the lens unit according to example 20.
FIG. 20E is a field curvature diagram for illustrating the lens unit according to example 20.

FNO = 4.141
Focal length of entire unit: f = 1 mm, image height = 0.939 mm, object distance = 18.1 mm, angle of view = 127.41°
Fr = 1.830 mm,
Ff = −1.235 mm,
fl = −0.782 mm FIG. 20A is a configuration diagram of the lens unit 20 according to the present example, and FIGS. 20B to 20E are aberration diagrams of the lens unit 20.

EXAMPLE 21

Numerical data, etc. of optical members included in a lens unit 21 according to example 21 are indicated below.

TABLE 21

| | | | |
|---|---|---|---|
| r1 = ∞ | d1 = 0.5164 | n1 = 2.18246 | ν1 = 33.01 |
| r2 = 0.8569 | d2 = 0.5680 | n2 = 1.93429 | ν2 = 18.90 |
| r3 = ∞ | d3 = 0.6885 | n3 = 1.51564 | ν3 = 75.00 |
| r4 = −4.4337 | d4 = 0.1377 | n4 = 1.88815 | ν4 = 40.76 |
| r5 = ∞ | d5 = 0.5336 | n5 = 1.73234 | ν5 = 54.68 |
| r6 = ∞(STO) | d6 = 0.0516 | n6 = 1.93429 | ν6 = 18.90 |
| r7 = ∞ | d7 = 1.1807 | n7 = 1.51825 | ν7 = 64.14 |
| r8 = −1.9271 | d8 = 0.1893 | n8 = 1.61379 | ν8 = 50.20 |
| r9 = 4.6518 | d9 = 1.1188 | | |
| r10 = −1.2548 | d10 = 0.4092 | | |
| r11 = −8.2907 | d11 = 1.4631 | | |
| r12 = ∞ | d12 = 0.7000 | | |
| r13 = ∞ | d13 = 0.6885 | | |
| r14 = ∞ | | | |

Figure 21A:
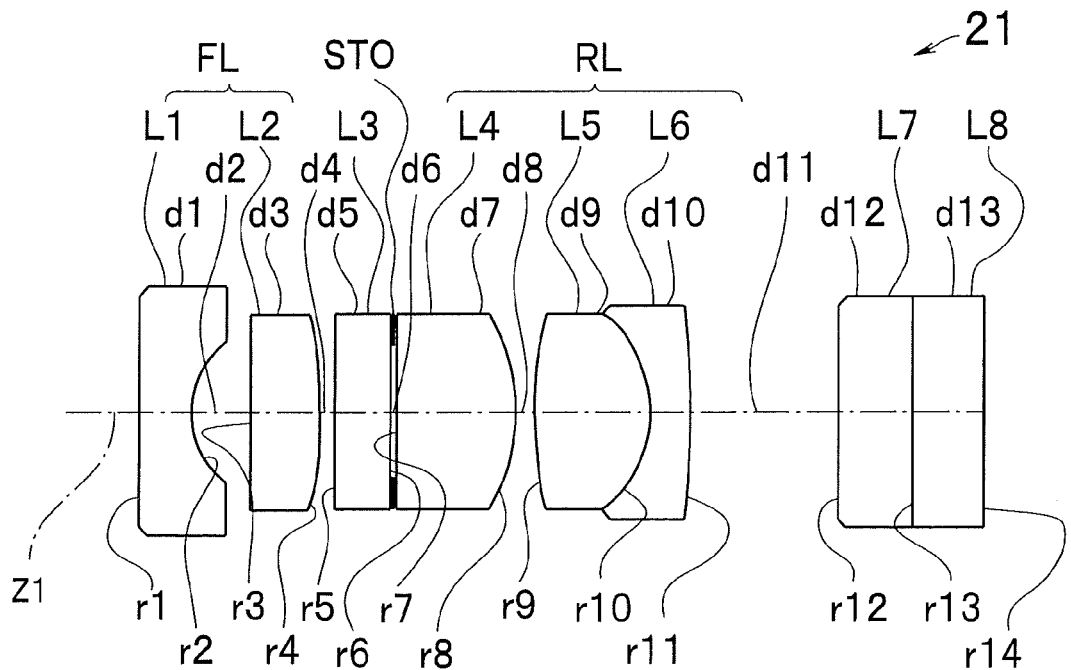
FIG. 21A is a cross-sectional diagram taken along an optical axis for illustrating a lens unit according to example 21.
Figures 21B, 21C, 21D, 21E:
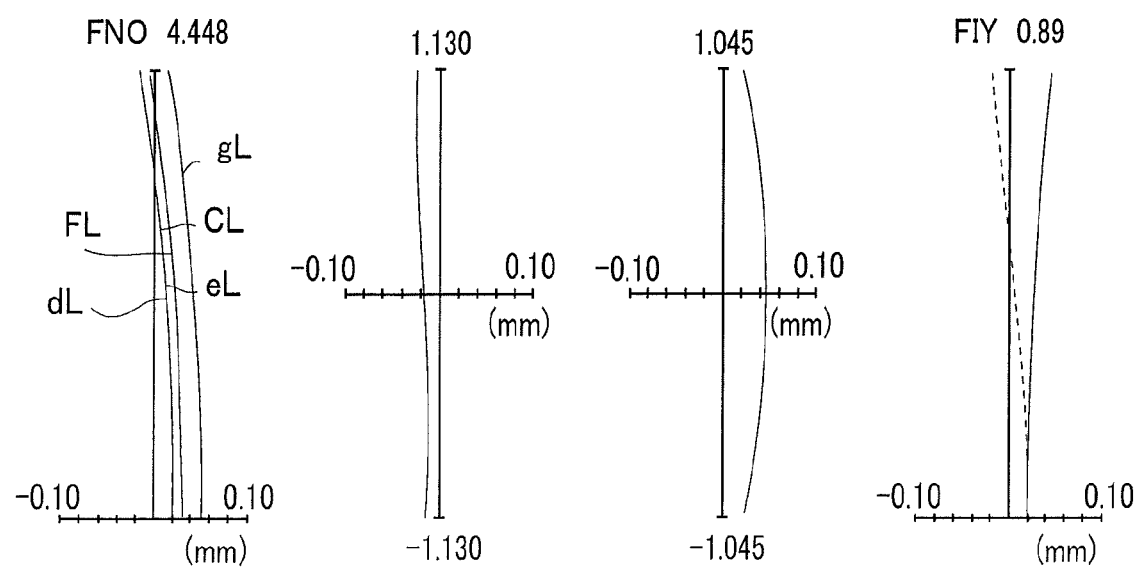
FIG. 21B is a spherical aberration diagram for illustrating the lens unit according to example 21.
FIG. 21C is a coma aberration diagram (M) for illustrating the lens unit according to example 21.
FIG. 21D is a coma aberration diagram (S) for illustrating the lens unit according to example 21.
FIG. 21E is a field curvature diagram for illustrating the lens unit according to example 21.

FNO = 4.448
Focal length of entire unit: f = 1 mm, image height = 0.893 mm, object distance = 17.2 mm, angle of view = 117.85°
Fr = 1.764 mm,
Ff = −1.110 mm,
fl = −0.725 mm FIG. 21A is a configuration diagram of the lens unit 21 according to the present example, and FIGS. 21B to 21E are aberration diagrams of the lens unit 21.

EXAMPLE 22

Numerical data, etc. of optical members included in a lens unit 22 according to example 22 are indicated below.

TABLE 22

| | | | |
|---|---|---|---|
| r1 = ∞ | d1 = 0.4583 | n1 = 2.18246 | ν1 = 33.01 |
| r2 = 0.7351 | d2 = 0.3564 | n2 = 1.85504 | ν2 = 23.78 |
| r3 = ∞ | d3 = 0.5199 | n3 = 1.51564 | ν3 = 75.00 |
| r4 = −4.1679 | d4 = 1.3580 | n4 = 1.83932 | ν4 = 37.16 |
| r5 = ∞ | d5 = 0.4857 | n5 = 1.59143 | ν5 = 61.14 |
| r6 = ∞(STO) | d6 = 0.0509 | n6 = 1.93429 | ν6 = 18.90 |
| r7 = ∞ | d7 = 1.1253 | n7 = 1.51825 | ν7 = 64.14 |
| r8 = −1.6538 | d8 = 0.1867 | n8 = 1.61379 | ν8 = 50.20 |
| r9 = 3.6894 | d9 = 1.0133 | | |
| r10 = −1.2375 | d10 = 0.4035 | | |
| r11 = −3.4546 | d11 = 1.6970 | | |
| r12 = ∞ | d12 = 0.7127 | | |
| r13 = ∞ | d13 = 0.6788 | | |
| r14 = ∞ | | | |

Figure 22A:
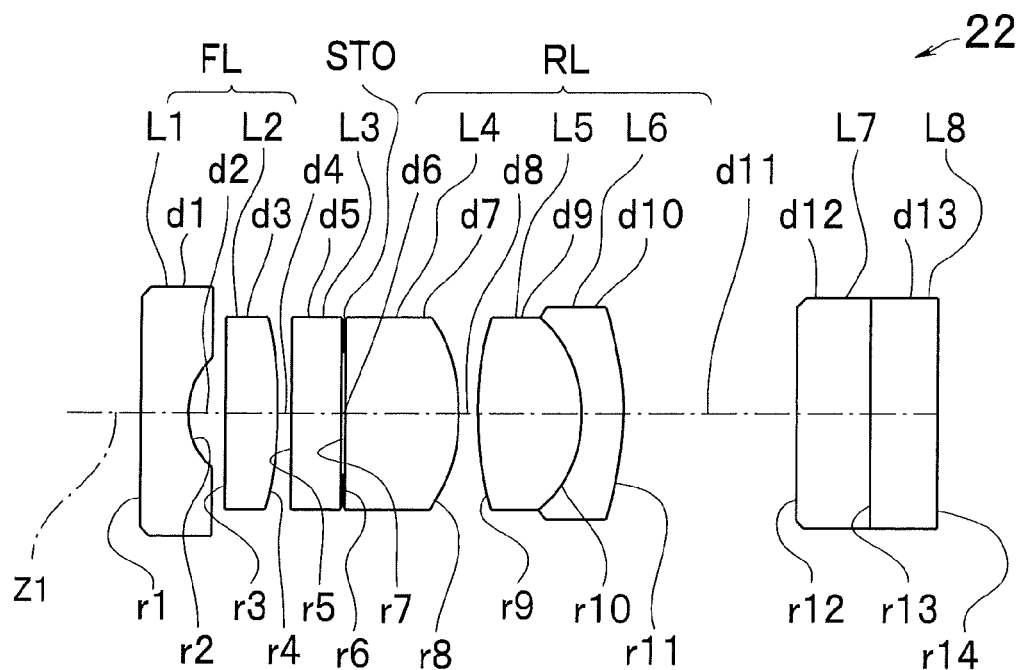
FIG. 22A is a cross-sectional diagram taken along an optical axis for illustrating a lens unit according to example 22.
Figures 22B, 22C, 22D, 22E:
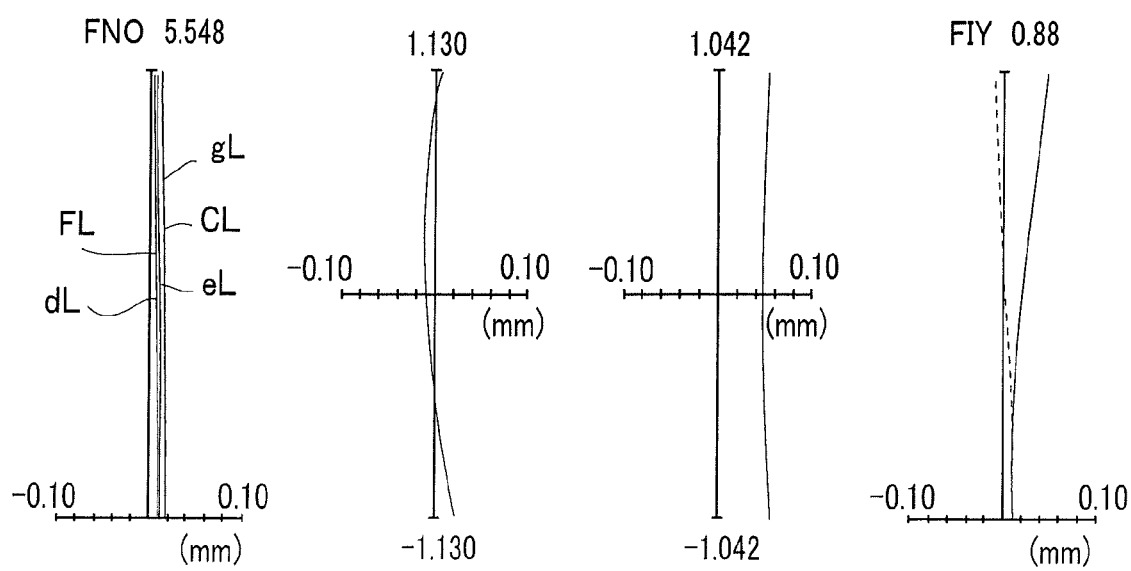
FIG. 22B is a spherical aberration diagram for illustrating the lens unit according to example 22.
FIG. 22C is a coma aberration diagram (M) for illustrating the lens unit according to example 22.
FIG. 22D is a coma aberration diagram (S) for illustrating the lens unit according to example 22.
FIG. 22E is a field curvature diagram for illustrating the lens unit according to example 22.

FNO = 5.548
Focal length of entire unit: f = 1 mm, image height = 0.881 mm, object distance = 17.01 mm, angle of view = 115.4°
Fr = 1.612 mm,
Ff = −0.838 mm,
fl = −0.622 mm FIG. 22A is a configuration diagram of the lens unit 22 according to the present example, and FIGS. 22B to 22E are aberration diagrams of the lens unit 22.

EXAMPLE 23

Numerical data, etc. of optical members included in a lens unit 23 according to example 23 are indicated below.

TABLE 23

| | | | |
|---|---|---|---|
| r1 = ∞ | d1 = 0.5000 | n1 = 2.18246 | ν1 = 33.01 |
| r2 = 1.0234 | d2 = 0.4160 | n2 = 1.93429 | ν2 = 18.90 |
| r3 = ∞ | d3 = 0.7234 | n3 = 1.51564 | ν3 = 75.00 |
| r4 = −5.2110 | d4 = 0.0543 | n4 = 1.88815 | ν4 = 40.76 |
| r5 = ∞ | d5 = 0.5606 | n5 = 1.73234 | ν5 = 54.68 |
| r6 = ∞(STO) | d6 = 0.1447 | n6 = 1.93429 | ν6 = 18.90 |
| r7 = −7.9337 | d7 = 1.3989 | n7 = 1.51825 | ν7 = 64.14 |
| r8 = −1.9816 | d8 = 0.1989 | n8 = 1.61379 | ν8 = 50.20 |
| r9 = 11.4247 | d9 = 1.1756 | | |
| r10 = −1.3087 | d10 = 0.4300 | | |
| r11 = −2.8801 | d11 = 1.8085 | | |
| r12 = ∞ | d12 = 0.7505 | | |
| r13 = ∞ | d13 = 0.7234 | | |
| r14 = ∞ | | | |

Figure 23A:
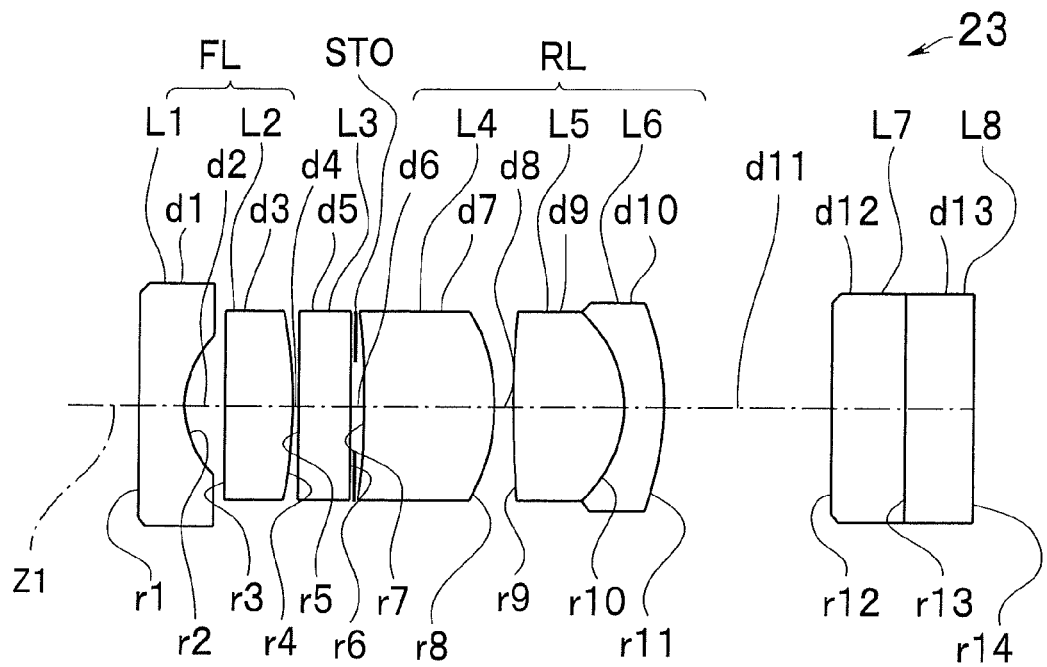
FIG. 23A is a cross-sectional diagram taken along an optical axis for illustrating a lens unit according to example 23.
Figures 23B, 23C, 23D, 23E:
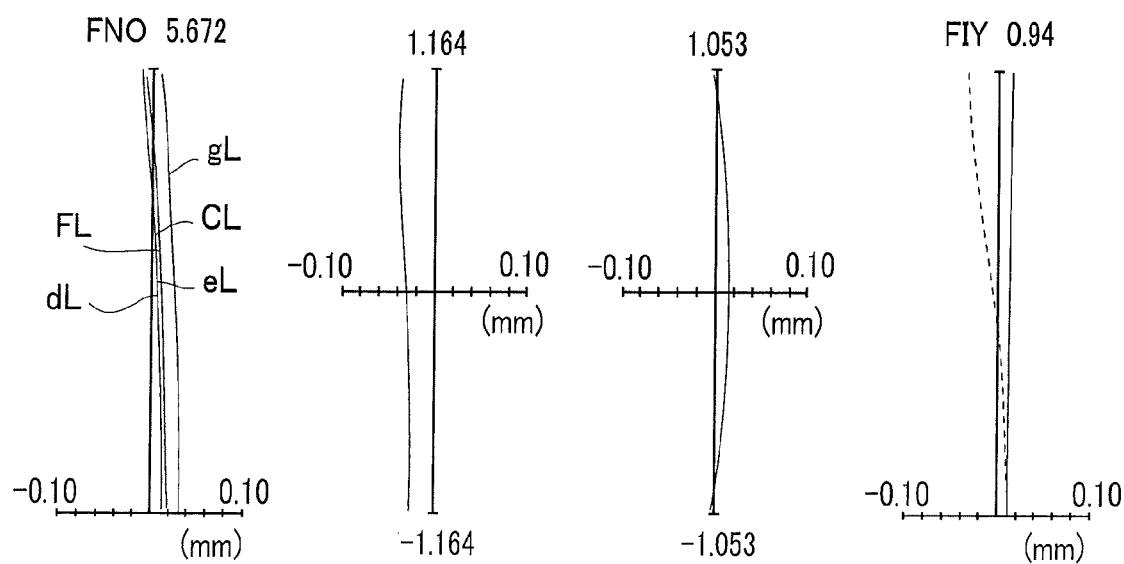
FIG. 23B is a spherical aberration diagram for illustrating the lens unit according to example 23.
FIG. 23C is a coma aberration diagram (M) for illustrating the lens unit according to example 23.
FIG. 23D is a coma aberration diagram (S) for illustrating the lens unit according to example 23.
FIG. 23E is a field curvature diagram for illustrating the lens unit according to example 23.

FNO = 5.672
Focal length of entire unit: f = 1 mm, image height = 0.939 mm, object distance = 18 mm, angle of view = 127.86°
Fr = 1.868 mm,
Ff = −1.231 mm,
fl = −0.865 mm FIG. 23A is a configuration diagram of the lens unit 23 according to the present example, and FIGS. 23B to 23E are aberration diagrams of the lens unit 23.

EXAMPLE 24

Numerical data, etc. of optical members included in a lens unit 24 according to example 24 are indicated below.

TABLE 24

| | | | |
|---|---|---|---|
| r1 = ∞ | d1 = 0.5429 | n1 = 2.18246 | ν1 = 33.01 |
| r2 = 1.0687 | d2 = 0.4162 | n2 = 1.93429 | ν2 = 18.90 |
| r3 = −36.1952 | d3 = 0.7239 | n3 = 1.51564 | ν3 = 75.00 |
| r4 = −4.6981 | d4 = 0.0543 | n4 = 1.88815 | ν4 = 40.76 |
| r5 = ∞ | d5 = 0.5610 | n5 = 1.73234 | ν5 = 54.68 |
| r6 = ∞(STO) | d6 = 0.1448 | n6 = 1.93429 | ν6 = 18.90 |
| r7 = −5.7493 | d7 = 1.4630 | n7 = 1.51825 | ν7 = 64.14 |
| r8 = −1.9553 | d8 = 0.1991 | n8 = 1.61379 | ν8 = 50.20 |
| r9 = 15.0851 | d9 = 1.1763 | | |
| r10 = −1.2907 | d10 = 0.4303 | | |
| r11 = −2.7220 | d11 = 1.9002 | | |
| r12 = ∞ | d12 = 0.7400 | | |
| r13 = ∞ | d13 = 0.7239 | | |
| r14 = ∞ | | | |

Figure 24A:
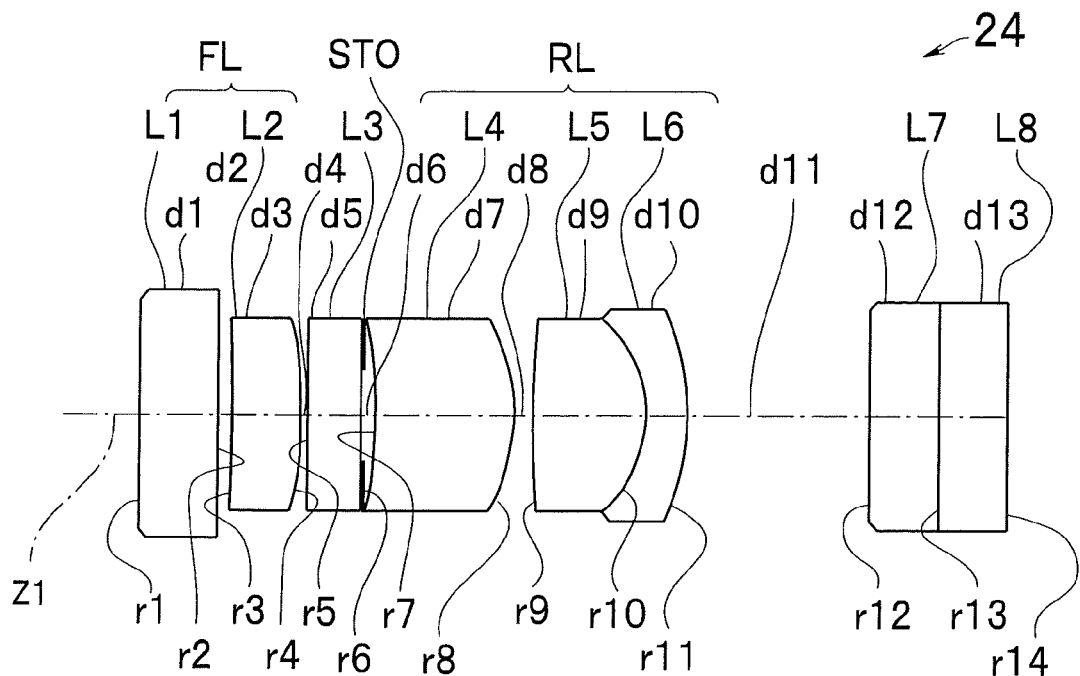
FIG. 24A is a cross-sectional diagram taken along an optical axis for illustrating a lens unit according to example 24.
Figures 24B, 24C, 24D, 24E:
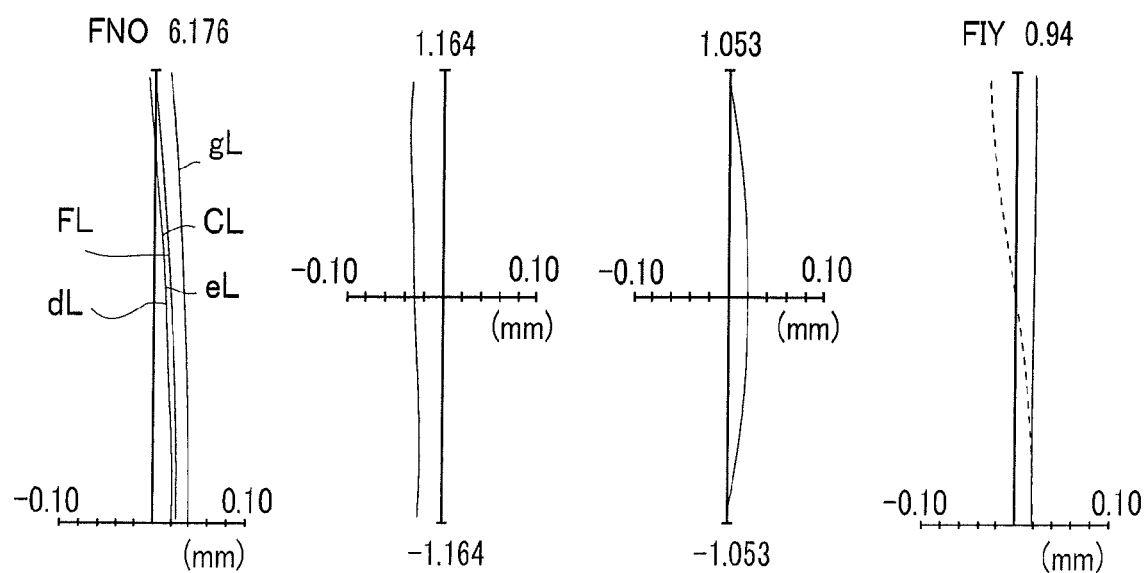
FIG. 24B is a spherical aberration diagram for illustrating the lens unit according to example 24.
FIG. 24C is a coma aberration diagram (M) for illustrating the lens unit according to example 24.
FIG. 24D is a coma aberration diagram (S) for illustrating the lens unit according to example 24.

FNO = 6.176
Focal length of entire unit: f = 1 mm, image height = 0.939 mm, object distance = 18.098 mm, angle of view = 128.03°
Fr = 1.894 mm,
Ff = −1.301 mm,
fl = −0.904 mm FIG. 24A is a configuration diagram of the lens unit 24 according to the present example, and FIGS. 24B to 24E are aberration diagrams of the lens unit 24.

EXAMPLE 25

Numerical data, etc. of optical members included in a lens unit 25 according to example 25 are indicated below.

TABLE 25

| | | | |
|---|---|---|---|
| r1 = ∞ | d1 = 0.3920 | n1 = 2.18246 | ν1 = 33.01 |
| r2 = 1.0035 | d2 = 0.3395 | n2 = 1.93429 | ν2 = 18.90 |
| r3 = 19.3992 | d3 = 0.5820 | n3 = 1.88815 | ν3 = 40.76 |
| r4 = −4.4012 | d4 = 0.5308 | n4 = 1.73234 | ν4 = 54.68 |
| r5 = ∞(STO) | d5 = 0.4829 | n5 = 1.93429 | ν5 = 18.90 |
| r6 = −11.6039 | d6 = 0.5453 | n6 = 1.51825 | ν6 = 64.10 |
| r7 = −1.7296 | d7 = 0.0485 | | |
| r8 = 15.3992 | d8 = 0.9673 | | |
| r9 = −1.1572 | d9 = 0.3696 | | |
| r10 = −2.7323 | d10 = 1.7957 | | |
| r11 = ∞ | d11 = 0.9099 | | |
| r12 = ∞ | | | |

Figure 25A:
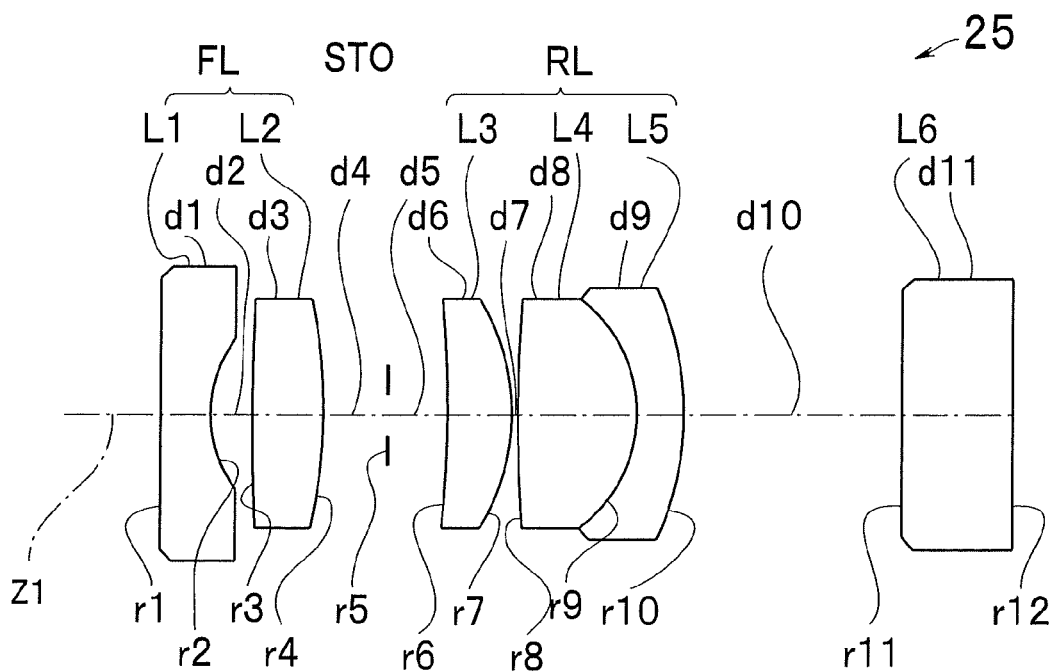
Figures 25B, 25C, 25D, 25E:
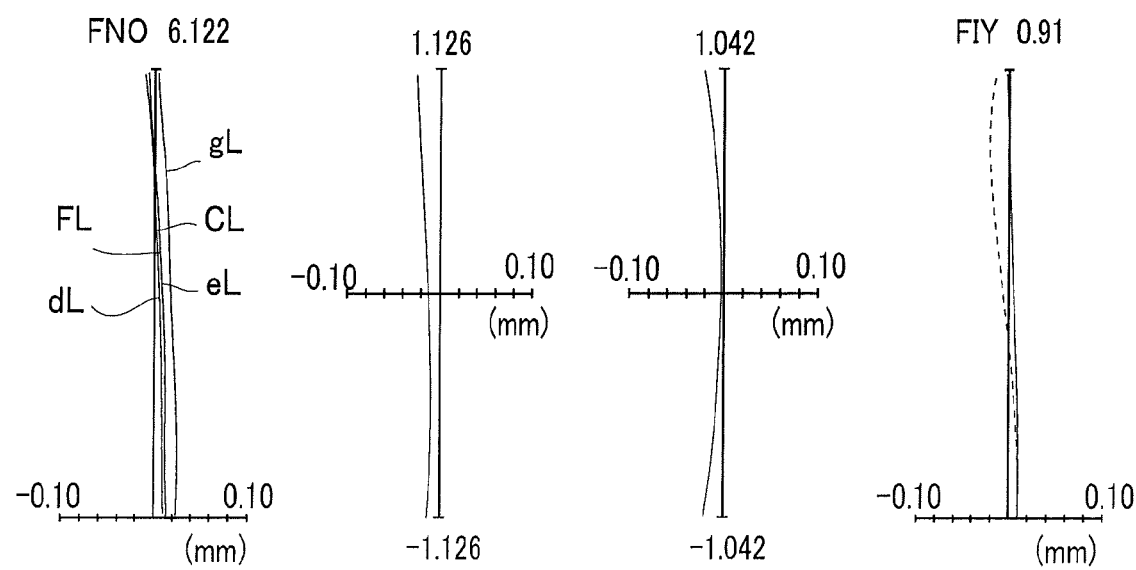

FNO = 6.122
Focal length of entire unit: f = 1 mm, image height = 0.913 mm, object distance = 18.93 mm, angle of view = 123.19°
Fr = 1.687 mm,
Ff = −1.346 mm,
fl = −0.849 mm FIG. 25A is a configuration diagram of the lens unit 25 according to the present example, and FIGS. 25B to 25E are aberration diagrams of the lens unit 25.

EXAMPLE 26

Numerical data, etc. of optical members included in a lens unit 26 according to example 26 are indicated below.

TABLE 26

| | | | |
|---|---|---|---|
| r1 = ∞ | d1 = 0.5010 | n1 = 2.01169 | ν1 = 28.27 |
| r2 = 0.8712 | d2 = 0.4166 | n2 = 1.93429 | ν2 = 18.90 |
| r3 = ∞ | d3 = 0.5993 | n3 = 1.51564 | ν3 = 75.00 |
| r4 = −8.5465 | d4 = 0.1449 | n4 = 1.88815 | ν4 = 40.76 |
| r5 = ∞ | d5 = 0.4554 | n5 = 1.73234 | ν5 = 54.68 |
| r6 = ∞(STO) | d6 = 0.0543 | n6 = 1.93429 | ν6 = 18.90 |
| r7 = ∞ | d7 = 1.8080 | n7 = 1.51825 | ν7 = 64.14 |
| r8 = −2.0398 | d8 = 0.1993 | n8 = 1.61379 | ν8 = 50.20 |
| r9 = 4.5503 | d9 = 1.1775 | | |
| r10 = −1.4905 | d10 = 0.4307 | | |
| r11 = −5.8142 | d11 = 1.4790 | | |

TABLE 26-continued

| | |
|---|---|
| r12 = ∞ | d12 = 0.7246 |
| r13 = ∞ | d13 = 0.7246 |

Figure 26A:
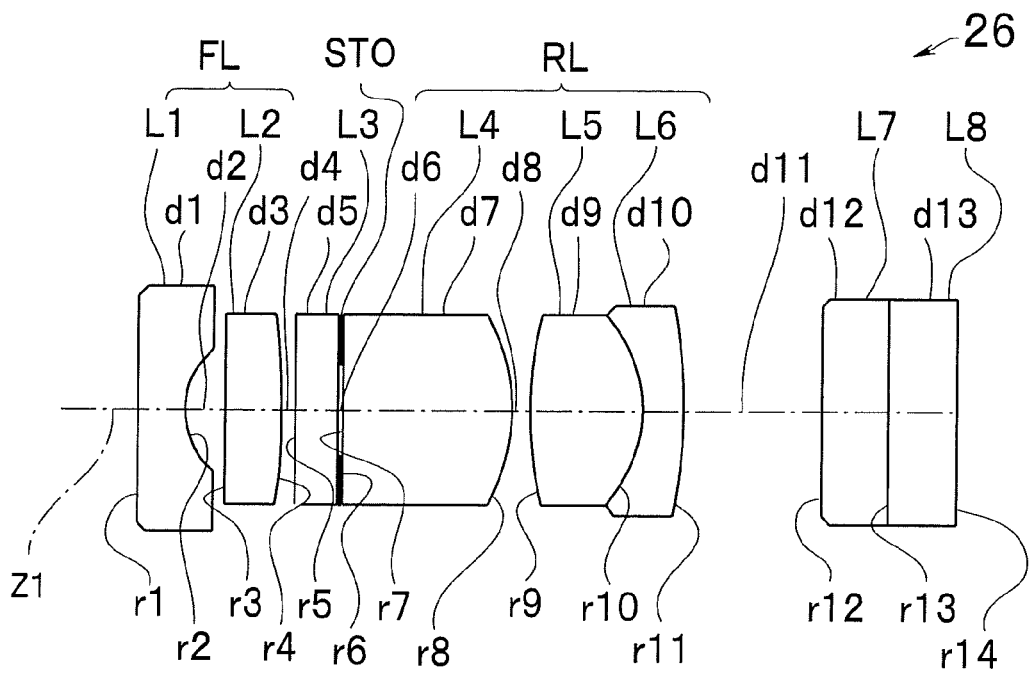
Figures 26B, 26C, 26D, 26E:
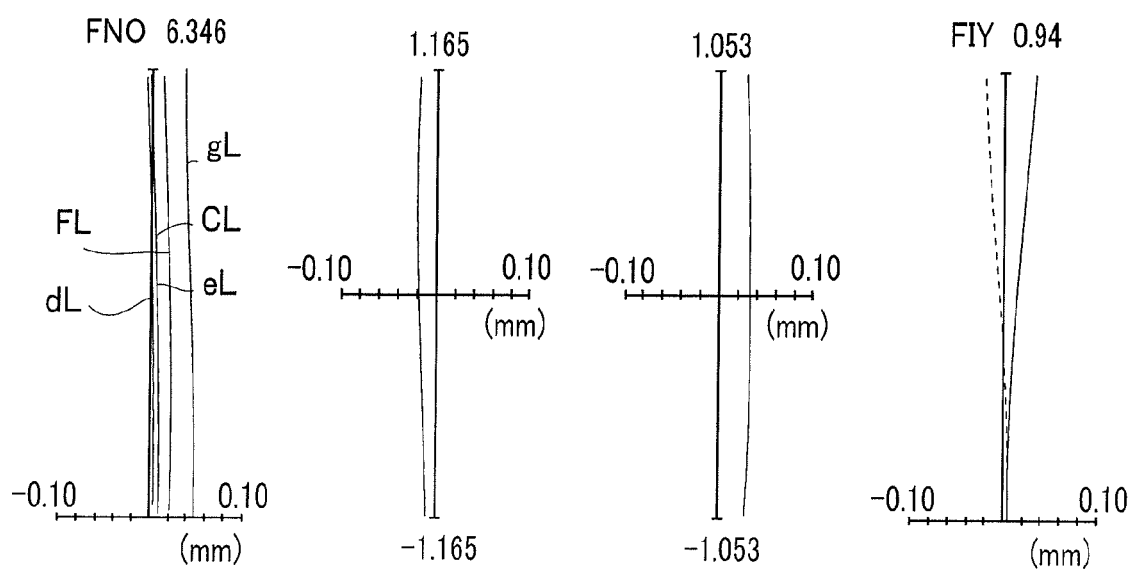

FNO = 6.346
Focal length of entire unit: f = 1 mm, image height = 0.94 mm, object distance = 18.116 mm, angle of view = 128.00°
Fr = 1.733 mm,
Ff = −1.042 mm,
fl = −0.861 mm FIG. 26A is a configuration diagram of the lens unit 26 according to the present example, and FIGS. 26B to 26E are aberration diagrams of the lens unit 26.

Summary of Examples 1 to 26

Tables 27 and 28 list respective configurations of the lens units according to examples 1 to 26. In Tables 27 and 28, configurations of lens units disclosed in Japanese Patent Application Laid-Open Publication No. 6-308381 are listed as comparative examples 1 to 3. In Table 2, a circle indicates that the relevant condition is satisfied, and x indicates that the relevant condition is not satisfied.

The lens units according to comparative example 1 to 3 have the following configurations, respectively:

Comparative example 1: f=1 mm, Fr=1.838 mm, Ff=−1.752 mm, fl=−1.020 mm
Comparative example 2: f=1 mm, Fr=1.877 mm, Ff=−1.812 mm, fl=−1.041 mm
Comparative example 3: f=1 mm, Fr=1.889 mm, Ff=−2.062 mm, fl=−0.808 mm

TABLE 27

| | SF | Fr/Ff | Ff/f | Ff/fl | n1 | Hk | n1 × Hk |
|---|---|---|---|---|---|---|---|
| Example 1 | −1.000 | −1.440 | −1.123 | 1.182 | 1.8882 | 710 | 1340.6 |
| Example 2 | −2.761 | −1.351 | −1.280 | 1.294 | 1.8882 | 710 | 1340.6 |
| Example 3 | −2.467 | −1.306 | −1.353 | 1.371 | 1.8882 | 710 | 1340.6 |
| Example 4 | −2.419 | −1.388 | −1.276 | 1.294 | 1.8882 | 710 | 1340.6 |
| Example 5 | −1.900 | −1.249 | −1.439 | 1.465 | 1.8882 | 710 | 1340.6 |
| Example 6 | −2.262 | −1.521 | −1.228 | 1.191 | 1.8882 | 710 | 1340.6 |
| Example 7 | −2.510 | −1.432 | −1.294 | 1.330 | 1.8882 | 710 | 1340.6 |
| Example 8 | −2.420 | −1.409 | −1.332 | 1.348 | 1.8882 | 710 | 1340.6 |
| Example 9 | −1.000 | −1.718 | −0.967 | 1.090 | 1.8882 | 710 | 1340.6 |
| Example 10 | −1.000 | −1.151 | −1.383 | 1.507 | 1.8882 | 710 | 1340.6 |
| Example 11 | −0.556 | −1.187 | −1.320 | 1.462 | 1.8882 | 710 | 1340.6 |
| Example 12 | −1.000 | −1.680 | −0.993 | 1.093 | 1.8882 | 710 | 1340.6 |
| Example 13 | −5.000 | −1.520 | −1.226 | 1.295 | 1.8882 | 710 | 1340.6 |
| Example 14 | −1.000 | −1.596 | −1.135 | 1.386 | 2.1825 | 1200 | 2617.0 |
| Example 15 | −1.000 | −1.561 | −1.174 | 1.445 | 2.1825 | 1200 | 2617.0 |
| Example 16 | −1.000 | −1.476 | −1.310 | 1.562 | 2.1825 | 1200 | 2617.0 |
| Example 17 | −1.000 | −1.742 | −1.129 | 1.283 | 2.1825 | 1200 | 2617.0 |
| Example 18 | −1.000 | −1.688 | −1.144 | 1.347 | 2.1825 | 1200 | 2617.0 |
| Example 19 | −1.000 | −1.756 | −1.000 | 1.250 | 2.1825 | 1200 | 2617.0 |
| Example 20 | −1.000 | −1.482 | −1.235 | 1.579 | 2.1825 | 1200 | 2617.0 |
| Example 21 | −1.000 | −1.588 | −1.110 | 1.532 | 2.1825 | 1200 | 2617.0 |
| Example 22 | −1.000 | −1.924 | −0.838 | 1.348 | 2.1825 | 1200 | 2617.0 |
| Example 23 | −1.000 | −1.518 | −1.231 | 1.422 | 2.1825 | 1200 | 2617.0 |
| Example 24 | −1.298 | −1.456 | −1.301 | 1.440 | 2.1825 | 1200 | 2617.0 |

TABLE 27-continued

|  | SF | Fr/Ff | Ff/f | Ff/f1 | n1 | Hk | n1 × Hk |
|---|---|---|---|---|---|---|---|
| Example 25 | −0.630 | −1.253 | −1.346 | 1.586 | 2.1825 | 1200 | 2617.0 |
| Example 26 | −1.000 | −1.663 | −1.042 | 1.210 | 2.0117 | 700 | 1408.2 |
| Comparative example 1 | −1.000 | −1.049 | −1.751 | 1.718 | 1.8882 | 710 | 1340.6 |
| Comparative example 2 | −1.000 | −1.036 | −1.812 | 1.740 | 1.8882 | 710 | 1340.6 |
| Comparative example 3 | −1.085 | 0.916 | 2.063 | 2.553 | 1.8882 | 710 | 1340.6 |

TABLE 28

|  | Condition (1) −6 < SF < 0 | Condition (2) −3 < (Fr/Ff) < −1.1 | Condition (3) −1.6 < (Ff/f) < −0.6 | Condition (4) (Ff/f1) < 1.6 | Condition (5) n1 > 2 | Condition (6) N1 × Hk > 2000 |
|---|---|---|---|---|---|---|
| Example 1 | ○ | ○ | ○ | ○ | X | X |
| Example 2 | ○ | ○ | ○ | ○ | X | X |
| Example 3 | ○ | ○ | ○ | ○ | X | X |
| Example 4 | ○ | ○ | ○ | ○ | X | X |
| Example 5 | ○ | ○ | ○ | ○ | X | X |
| Example 6 | ○ | ○ | ○ | ○ | X | X |
| Example 7 | ○ | ○ | ○ | ○ | X | X |
| Example 8 | ○ | ○ | ○ | ○ | X | X |
| Example 9 | ○ | ○ | ○ | ○ | X | X |
| Example 10 | ○ | ○ | ○ | ○ | X | X |
| Example 11 | ○ | ○ | ○ | ○ | X | X |
| Example 12 | ○ | ○ | ○ | ○ | X | X |
| Example 13 | ○ | ○ | ○ | ○ | X | X |
| Example 14 | ○ | ○ | ○ | ○ | X | X |
| Example 15 | ○ | ○ | ○ | ○ | ○ | ○ |
| Example 16 | ○ | ○ | ○ | ○ | ○ | ○ |
| Example 17 | ○ | ○ | ○ | ○ | ○ | ○ |
| Example 18 | ○ | ○ | ○ | ○ | ○ | ○ |
| Example 19 | ○ | ○ | ○ | ○ | ○ | ○ |
| Example 20 | ○ | ○ | ○ | ○ | ○ | ○ |
| Example 21 | ○ | ○ | ○ | ○ | ○ | ○ |
| Example 22 | ○ | ○ | ○ | ○ | ○ | ○ |
| Example 23 | ○ | ○ | ○ | ○ | ○ | ○ |
| Example 24 | ○ | ○ | ○ | ○ | ○ | ○ |
| Example 25 | ○ | ○ | ○ | ○ | ○ | ○ |
| Example 26 | ○ | ○ | ○ | ○ | ○ | X |
| Comparative example 1 | ○ | X | X | X | X | X |
| Comparative example 2 | ○ | X | X | X | X | X |
| Comparative example 3 | ○ | X | X | X | X | X |

From the above results, it is clear that the lens units according to the examples are effective. In other words, in comparative examples 1 to 3, a cementing surface of a cemented lens disposed in a rear lens group for correction of a chromatic aberration of magnification exhibits poor workability, and it is not easy to achieve the recent size reduction while correcting other aberrations such as a field curvature. Meanwhile, the aforementioned problems have been solved in the lens unit according to the examples. In other words, the lens units according to examples 1 to 25 provide only small chromatic aberration of magnification.

Furthermore, the lens units according to examples 13 to 25 satisfy condition (6), i.e., n1×Hk>2000, and thus, an outer surface lens (first lens L1) exhibits a high resistance to cracking and lens scratching compared to the lens units according to example 1 to 12.

EXAMPLE 27

Figure 27:
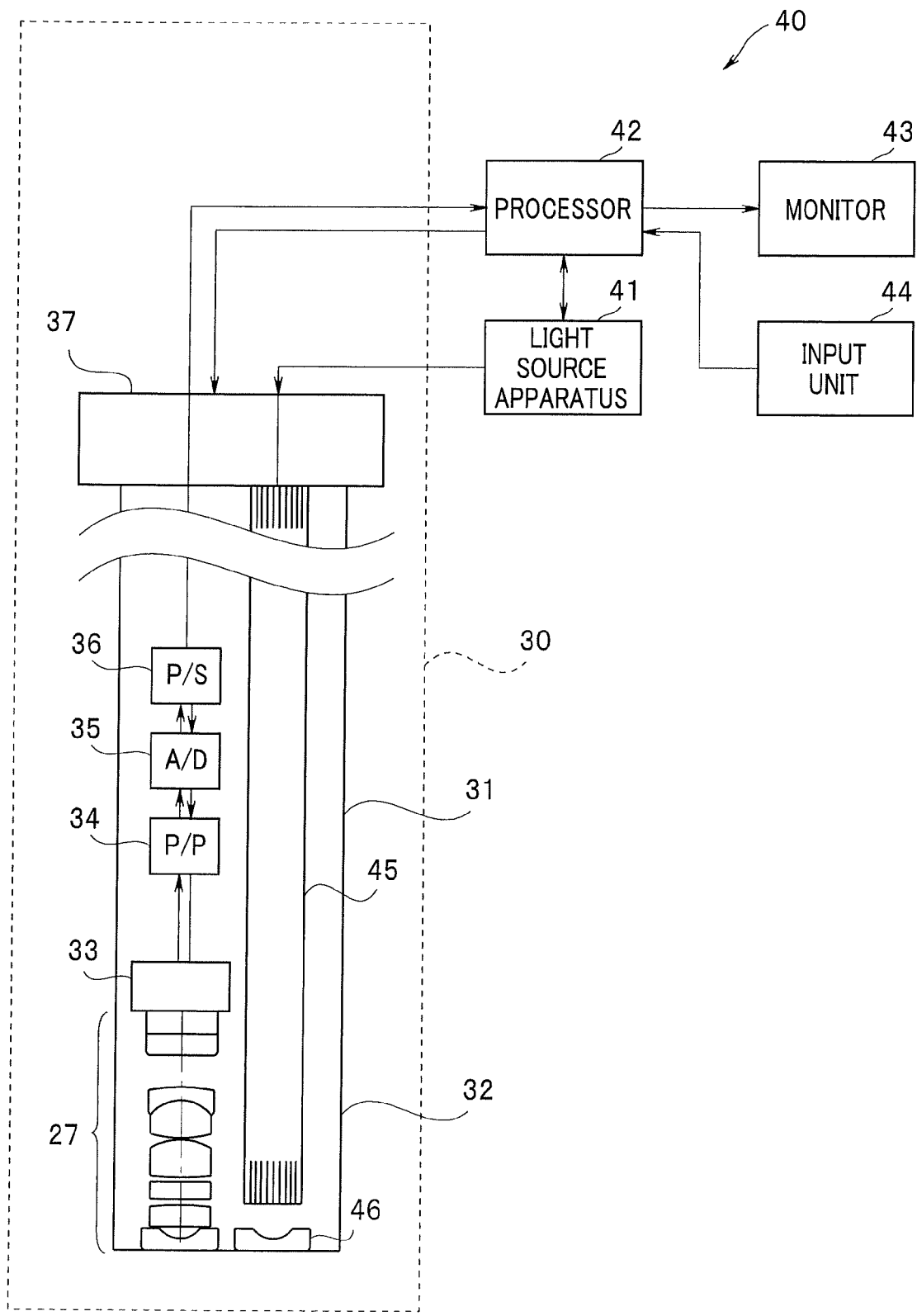

Next, an endoscope 30 including a lens unit 27 according to example 15 of the present invention will be described. An endoscope system 40, which is illustrated in FIG. 27, includes an endoscope 30 including an insertion portion 31 that is inserted into an inner portion of a body of a subject, a light source device 41 that illuminates the inner portion of the body, and a processor 42 that performs signal processing. In other words, a light guide fiber 45 that guides illuminating light from the light source device 41 to a distal end portion 32 is inserted in the insertion portion 31 and illuminates the inner portion of the body via an illumination optical system 32. The processor 42 can be used as an endoscope system adapted to various purposes by combining various endoscopes and/or various light source devices. Furthermore, the endoscope system 40 includes a monitor 43 that displays, e.g., an endoscopic image, and an input unit 44 such as a keyboard for a surgeon to perform, e.g., settings.

The endoscope 30 is an electronic endoscope including a CCD 33, which is an image pickup section that picks up a color endoscopic image, an pre-process (P/P) section 34, and an A/D conversion section 35 and a parallel/serial conversion (P/S) section 36, at the distal end portion 32 of the insertion portion 31 connected to an operation section 37. The lens unit 27 for forming an optical image and a CCD 33 for taking an image of the inner portion of the subject are disposed at the distal end portion 32. An endoscopic image taken by the CCD 33 is converted into digital signals and transmitted to the processor 42. For the image pickup section, e.g., a CMD (charged modulation device) image pickup device, a C-MOS image pickup device, an AMI (amplified MOS imager) or a BCCD (back illuminated CCD) may be employed instead of the CCD 33. Also, it is possible to use a black-and-white CCD instead of a color CCD and chronologically change illumination into RBG signals.

The lens unit 27 of the endoscope 30 has a configuration similar to that of, e.g., the lens unit 13 according to example 1, which has already been described. As already described, e.g., the lens unit 13 has a small diameter and exhibits excellent optical characteristics. Thus, the endoscope 30 has a small diameter and exhibits good characteristics in picked-up images. In other words, an image picked up by the image endoscope 30 has only small chromatic aberration of magnification.

Furthermore, as a material of a first lens L1 of the lens unit 27, a material including at least any component from among Zr, Y, Gd, Ta, Nb, La and Hf as a main component thereof and having a refractive index exceeding 2, for example, yttria-stabilized zirconia, is used. Thus, the first lens L1) has resistance to cracking and lens scratching. Furthermore, the lens unit 27 also has durability for a severe condition in a saturated water vapor-used sterilization system with a high temperature of around 140° C. and a high pressure, such as that in what is called autoclave sterilization.

The present invention is not limited to the above-described embodiments, and various alterations, modifications and the like are possible as long as such alterations and modifications do not change the spirit of the present invention.

What is claimed is:

1. An endoscope objective lens unit comprising a front lens group and a rear lens group with an aperture stop interposed therebetween,
   wherein the front lens group includes a first lens having a negative refractive power and a second lens having a positive refractive power in this order from an object side,
   wherein the rear lens group includes a third lens having a positive refractive power, and a fourth lens having a positive refractive power and a fifth lens having a negative refractive power, the fourth lens and the fifth lens being cemented to each other, and
   wherein the endoscope objective lens unit satisfies expressions (1A), (2), (3) and (4) below:

$$-3 < SF \leq -1; \tag{1A}$$

$$-3.0 < Fr/Ff < -1.1; \tag{2}$$

$$-1.6 < Ff/f < -0.6; \text{ and} \tag{3}$$

$$Ff/f1 < 1.6, \tag{4}$$

where SF is a shape factor of (R2+R1)/(R2−R1), in which R1 is an object-side radius of curvature of the second lens and R2 is an image-side radius of curvature of the second lens, Ff is a focal length of the front lens group, Fr is a focal length of the rear lens group, f is a focal length of the entire unit, and f1 is a focal length of the first lens.

2. The endoscope objective lens unit according to claim 1, wherein a refractive index n1 (for an e-line) of a material of the first lens satisfies expression (5) below:

$$n1 > 2. \tag{5}$$

3. The endoscope objective lens unit according to claim 2, wherein the material of the first lens satisfies expression (6) below:

$$n1 \times Hk > 2000, \tag{6}$$

where n1 is a refractive index (for an e-line) and Hk is a Knoop hardness (N/mm²).

4. The endoscope objective lens unit according to claim 3, wherein the material of the first lens includes yttria-stabilized zirconia.

5. An endoscope comprising an endoscope objective lens unit, and an image pickup device that picks up an image formed by the endoscope objective lens unit,
   wherein the endoscope objective lens unit includes a front lens group and a rear lens group with an aperture stop interposed therebetween,
   wherein the front lens group includes a first lens having a negative refractive power and a second lens having a positive refractive power in this order from an object side,
   wherein the rear lens group includes a third lens having a positive refractive power, and a fourth lens having a positive refractive power and a fifth lens having a negative refractive power, the fourth lens and the fifth lens being cemented to each other, and
   wherein the endoscope objective lens unit satisfies expressions (1A), (2), (3) and (4) below:

$$-3 < SF \leq -1; \tag{1A}$$

$$-3.0 < Fr/Ff < -1.1; \tag{2}$$

$$-1.6 < Ff/f < 0.6; \text{ and} \tag{3}$$

$$Ff/f1 < 1.6, \tag{4}$$

where SF is a shape factor of (R2+R1)/(R2−R1), in which R1 is an object-side radius of curvature of the second lens and R2 is an image-side radius of curvature of the second lens, Ff is a focal length of the front lens group, Fr is a focal length of the rear lens group, f is a focal length of the entire unit, and f1 is a focal length of the first lens.

6. The endoscope according to claim 5, wherein a refractive index n1 (for an e-line) of a material of the first lens satisfies expression (5) below:

$$n1 > 2. \tag{5}$$

7. The endoscope according to claim 6, wherein the material of the first lens satisfies expression (6) below:

$$n1 \times Hk > 2000, \tag{6}$$

where n1 is a refractive index (for an e-line) and Hk is a Knoop hardness (N/mm²).

8. The endoscope according to claim 7, wherein the material of the first lens includes yttria-stabilized zirconia.

* * * * *